US012673061B2

(12) United States Patent
Miao et al.

(10) Patent No.: US 12,673,061 B2
(45) Date of Patent: Jul. 7, 2026

(54) UNIT DOSAGE COMPOSITION OF AKT INHIBITOR

(71) Applicant: NANJING CHIA TAI TIANQING PHARMACEUTICAL CO., LTD., Nanjing (CN)

(72) Inventors: Lei Miao, Nanjing (CN); Ying Tang, Nanjing (CN); He Tian, Nanjing (CN); Changyou Ma, Nanjing (CN); Jian Wu, Nanjing (CN); Dan Xu, Nanjing (CN); Chunxia Zhu, Nanjing (CN); Zhoushan Tian, Nanjing (CN)

(73) Assignee: NANJING CHIA TAI TIANQING PHARMACEUTICAL CO., LTD., Nanjing (CN)

( * ) Notice: Subject to any disclaimer, the term of this patent is extended or adjusted under 35 U.S.C. 154(b) by 574 days.

(21) Appl. No.: 18/017,416

(22) PCT Filed: Jul. 22, 2021

(86) PCT No.: PCT/CN2021/107810

§ 371 (c)(1), (2) Date: Jan. 23, 2023

(87) PCT Pub. No.: WO2022/017446

PCT Pub. Date: Jan. 27, 2022

(65) Prior Publication Data

US 2023/0321108 A1 Oct. 12, 2023

(30) Foreign Application Priority Data

Jul. 22, 2020 (CN) ......................... 202010709847.2

(51) Int. Cl.

| | |
|---|---|
| ***A61K 31/5365*** | (2006.01) |
| ***A61K 9/48*** | (2006.01) |
| ***A61K 31/519*** | (2006.01) |
| ***A61P 35/00*** | (2006.01) |

(52) U.S. Cl.

CPC .......... *A61K 31/5365* (2013.01); *A61K 9/485* (2013.01); *A61K 9/4858* (2013.01); *A61K 31/519* (2013.01); *A61P 35/00* (2018.01)

(58) Field of Classification Search

CPC ..... A61P 35/00; A61K 31/5365; A61K 9/485; A61K 9/4858; A61K 31/519

See application file for complete search history.

(56) References Cited

U.S. PATENT DOCUMENTS

2022/0144821 A1* 5/2022 Ma ........................ C07D 519/00
2023/0271958 A1* 8/2023 Wu ......................... A61P 35/00 514/252.16
2023/0286979 A1* 9/2023 Ma .......................... A61P 35/00

FOREIGN PATENT DOCUMENTS

| | | | |
|---|---|---|---|
| CN | 1882347 | A | 12/2006 |
| CN | 101511842 | A | 8/2009 |
| CN | 101578273 | A | 11/2009 |
| CN | 101631778 | A | 1/2010 |
| CN | 101970415 | A | 2/2011 |
| CN | 102574852 | A | 7/2012 |
| CN | 104744475 | A | 7/2015 |
| WO | 2020156437 | A1 | 8/2020 |

OTHER PUBLICATIONS

Translation of the Written Opinion of the International Searching Authority for PCT/CN2021/107810 (Year: 2022).*

* cited by examiner

*Primary Examiner* — James H Alstrum-Acevedo
*Assistant Examiner* — Carolyn L. Ladd
(74) *Attorney, Agent, or Firm* — Bayramoglu Law Offices LLC

(57) ABSTRACT

A unit dosage composition of an AKT inhibitor, and in particular, relates to a pharmaceutical composition in unit dosage form includes a compound of formula I-0 or a pharmaceutically acceptable salt thereof, wherein the mass of the compound I-0 or the pharmaceutically acceptable salt thereof is 5 mg to 400 mg calculated as free base.

I-0

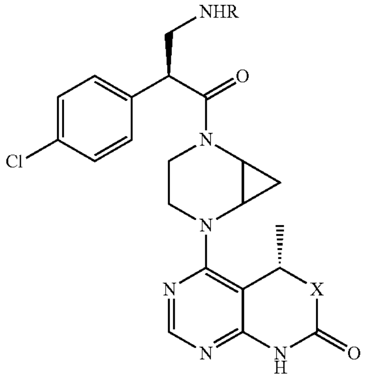

21 Claims, 3 Drawing Sheets

UNIT DOSAGE COMPOSITION OF AKT INHIBITOR

CROSS REFERENCE TO THE RELATED APPLICATIONS

This application is the national phase entry of International Application No. PCT/CN2021/107810, filed on Jul. 22, 2021, which is based upon and claims priority to Chinese Patent Application No. 202010709847.2, filed on Jul. 22, 2020, the entire contents of which are incorporated herein by reference.

TECHNICAL FIELD

The present application belongs to the field of medicinal chemistry, and specifically relates to a unit dosage composition of an AKT inhibitor, and a preparation method and medical use thereof.

BACKGROUND

The PI3K/AKT/mTOR pathway consisting of phosphoinositide-3-kinase (PI3K) and its downstream protein AKT (also known as protein kinase B, PKB), and mammalian target of Rapamycin (mTOR) as a very important intracellular signal transduction pathway, the pathway exerts an extremely important biological function in the process of cell growth, survival, proliferation, apoptosis, angiogenesis, autophagy, etc. Abnormal activation of the pathway will cause a series of diseases such as cancer, neuropathy, autoimmune disease, and hemolymphatic system disease.

AKT is a type of serine/threonine kinase and affects the survival, growth, metabolism, proliferation, migration, and differentiation of cell through numerous downstream effectors. Overactivation of AKT has been observed in more than 50% of human tumors, especially in prostate cancer, pancreatic cancer, bladder cancer, ovarian cancer, and breast cancer. Overactivation of AKT may lead to the formation, metastasis, and drug resistance of tumor. AKT has three isoforms: AKT1, AKT2, and AKT3. As a typical protein kinase, each isoform consists of an amino-terminal pleckstrin homology (PH) domain, a middle ATP-binding kinase domain, and a carboxyl-terminal regulatory domain. About 80% amino acid sequences of the three isoforms are homologous, and only the amino acid sequences in a binding domain between the PH domain and the kinase domain changes greatly.

The current drugs targeting the PI3K/AKT/mTOR signaling pathway mainly include PI3K inhibitors and mTOR inhibitors, while AKT is at the core of the signal transduction pathway. Inhibition of the AKT activity can not only avoid the severe side effects caused by inhibition of upstream PI3K, but also avoid the negative feedback mechanism caused by inhibition of downstream mTOR from affecting the efficacy of a drug. Therefore, development of effective and selective AKT inhibitor is an important direction for current development of tumor-targeting drugs. CN101631778A discloses a class of cyclopenta[D]pyrimidine derivatives, CN101578273A discloses a class of hydroxylated and methoxylated cyclopenta[D]pyrimidine derivatives, CN101511842A discloses a class of dihydrofuro pyrimidine derivatives, CN101970415A discloses a class of 5H-cyclopenta[d]pyrimidine derivatives, and these compounds inhibit AKT1 with $IC_{50}$ less than 10 μM.

Therefore, there is still a need for developing novel AKT inhibitors and applying them to the treatment of diseases.

SUMMARY

In a first aspect, the present application provides a unit dose pharmaceutical composition comprising compound I-0 or a pharmaceutically acceptable salt thereof, the mass of compound I-0 or the pharmaceutically acceptable salt thereof is 5 mg to 400 mg calculated as free base, and compound I-0 has the following structure:

I-0

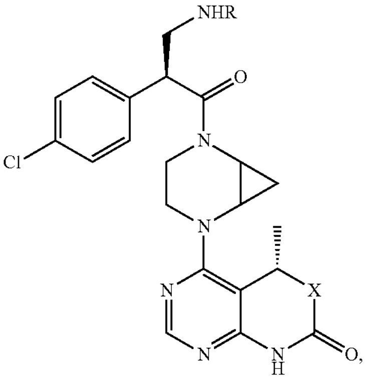

wherein, R is selected from C1-C4 alkyl or C3-C6 cycloalkyl; and

X is selected from $CH_2$ or O.

In some embodiments, R is selected from methyl, ethyl, n-propyl, isopropyl, tert-butyl, cyclopropyl, cyclopentyl or cyclohexyl.

In some typical embodiments, R is selected from methyl, ethyl, isopropyl or cyclopropyl.

In some more typical embodiments, R is selected from isopropyl or cyclopropyl.

In some embodiments, X is $CH_2$.

In some embodiments, X is O.

In some embodiments, compound I-0 is selected from the following compounds:

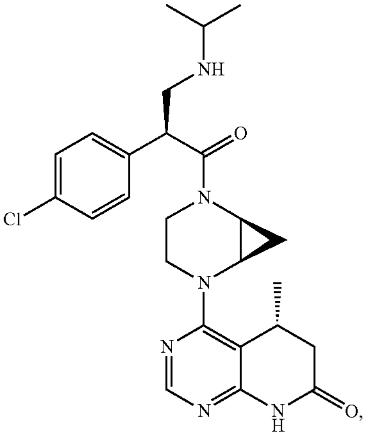

,

-continued

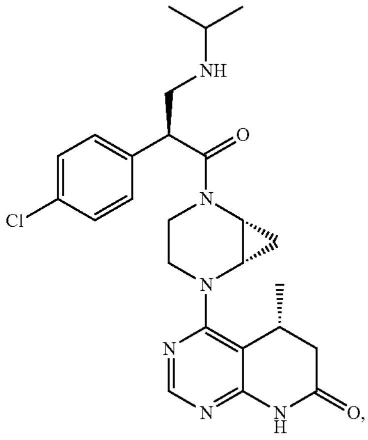
,

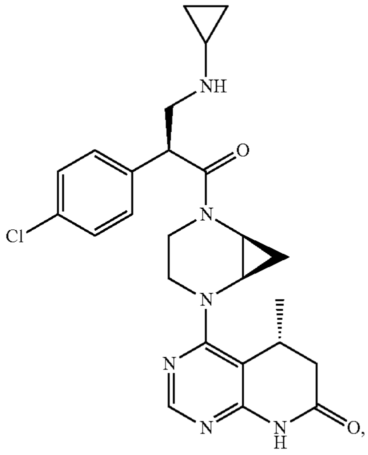
,

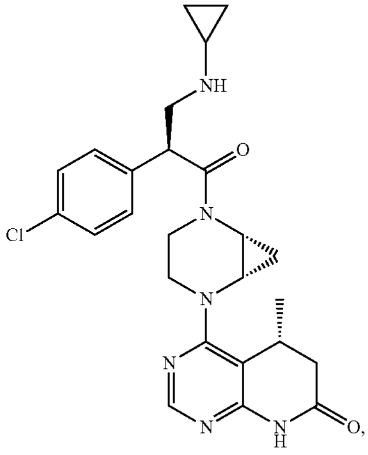
,

-continued

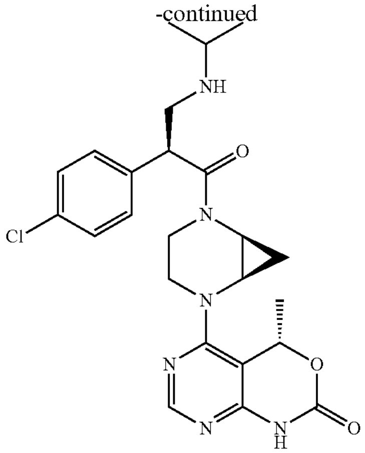
or

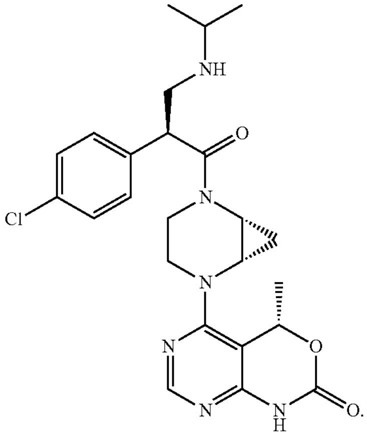
.

In some embodiments, in the unit dosage pharmaceutical composition, the mass of compound I-0 or a pharmaceutically acceptable salt thereof is 10 mg to 400 mg calculated as free base.

In some embodiments, in the unit dosage pharmaceutical composition, the mass of compound I-0 or a pharmaceutically acceptable salt thereof is 10 mg to 200 mg calculated as free base.

In some embodiments, in the unit dosage pharmaceutical composition, the mass of compound I-0 or a pharmaceutically acceptable salt thereof is 10 mg to 150 mg calculated as free base.

In some embodiments, in the unit dosage pharmaceutical composition, the mass of compound I-0 or a pharmaceutically acceptable salt thereof is 25 mg to 150 mg calculated as free base.

In some embodiments, in the unit dosage pharmaceutical composition, the mass of compound I-0 or a pharmaceutically acceptable salt thereof is 25 mg to 100 mg calculated as free base.

In some embodiments, in the unit dosage pharmaceutical composition, the mass of compound I-0 or a pharmaceutically acceptable salt thereof is 10 mg calculated as free base.

In some embodiments, in the unit dosage pharmaceutical composition, the mass of compound I-0 or a pharmaceutically acceptable salt thereof is 25 mg calculated as free base.

In some embodiments, in the unit dosage pharmaceutical composition, the mass of compound I-0 or a pharmaceutically acceptable salt thereof is 50 mg calculated as free base.

In some embodiments, in the unit dosage pharmaceutical composition, the mass of compound I-0 or a pharmaceutically acceptable salt thereof is 75 mg calculated as free base.

In some embodiments, in the unit dosage pharmaceutical composition, the mass of compound I-0 or a pharmaceutically acceptable salt thereof is 100 mg calculated as free base.

In some embodiments, in the unit dosage pharmaceutical composition, the mass of compound I-0 or a pharmaceutically acceptable salt thereof is 150 mg calculated as free base.

In some embodiments, in the unit dosage pharmaceutical composition, the mass of compound I-0 or a pharmaceutically acceptable salt thereof is 200 mg calculated as free base.

In some embodiments, in the unit dosage pharmaceutical composition, the mass of compound I-0 or a pharmaceutically acceptable salt thereof is 400 mg calculated as free base.

In some embodiments, calculated as free base, the mass of compound I-0 or the pharmaceutically acceptable salt thereof is 0.1-99.9% of the total mass of the pharmaceutical composition, preferably 5-90%, and more preferably 25-65%.

In another aspect, the present application provides a unit dosage pharmaceutical composition including compound I or a pharmaceutically acceptable salt thereof, the mass of compound I or a pharmaceutically acceptable salt thereof is 5 mg to 400 mg calculated as free base, and compound I has the following structure:

I

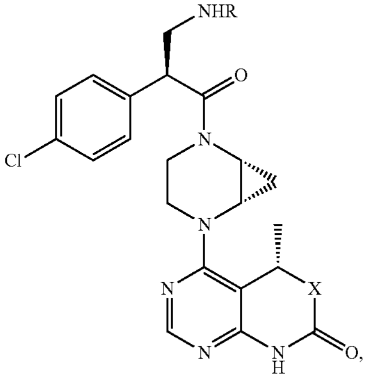

where, R is selected from C1-C4 alkyl or C3-C6 cycloalkyl; and

X is selected from $CH_2$ or O.

In some embodiments, R is selected from methyl, ethyl, n-propyl, isopropyl, tert-butyl, cyclopropyl, cyclopentyl or cyclohexyl.

In some typical embodiments, R is selected from methyl, ethyl, isopropyl or cyclopropyl.

In some more typical embodiments, R is selected from isopropyl or cyclopropyl.

In some embodiments, X is $CH_2$.

In some embodiments, X is O.

In some embodiments, compound I is selected from the following compounds:

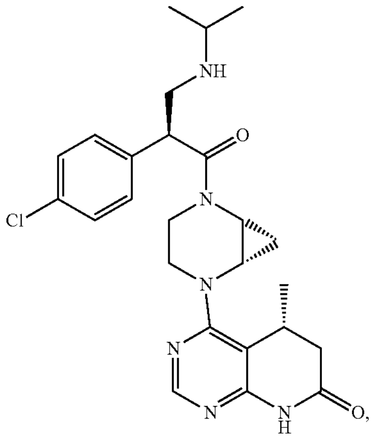

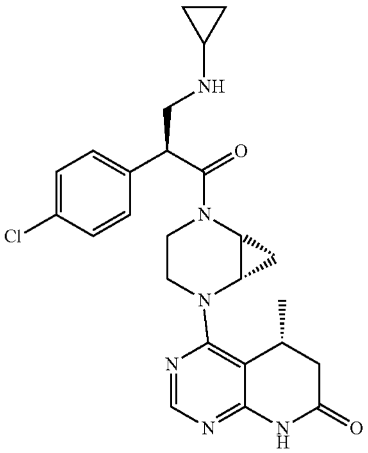

or

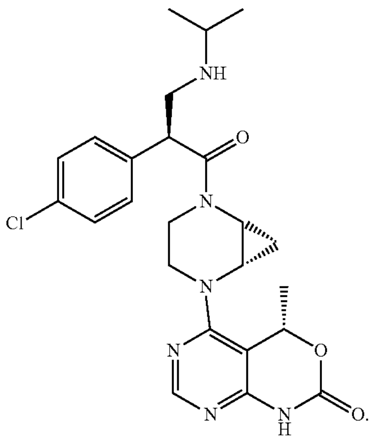

In some embodiments, compound I is the following compound:

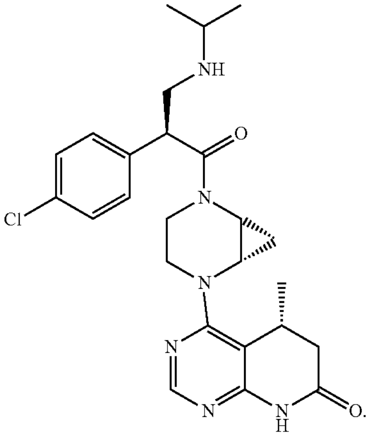

In some embodiments, compound I is the following compound:

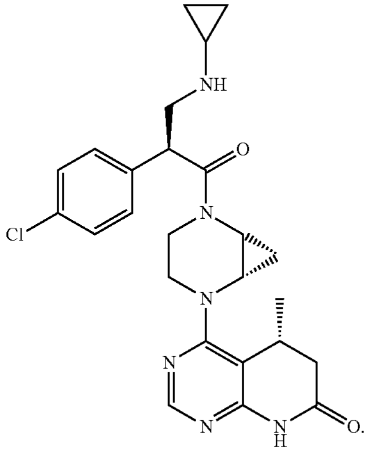

In some embodiments, compound I is the following compound:

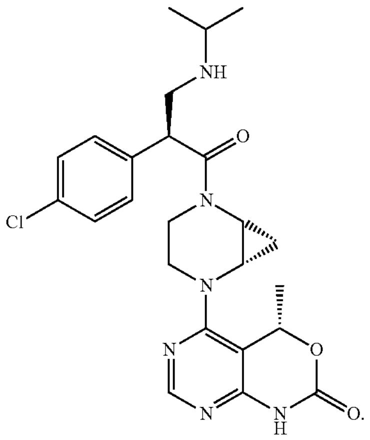

In some embodiments, in the unit dosage pharmaceutical composition, the mass of compound I or a pharmaceutically acceptable salt thereof is 10 mg to 400 mg calculated as free base.

In some embodiments, in the unit dosage pharmaceutical composition, the mass of compound I or a pharmaceutically acceptable salt thereof is 10 mg to 200 mg calculated as free base.

In some embodiments, in the unit dosage pharmaceutical composition, the mass of compound I or a pharmaceutically acceptable salt thereof is 10 mg to 150 mg calculated as free base.

In some embodiments, in the unit dosage pharmaceutical composition, the mass of compound I or a pharmaceutically acceptable salt thereof is 25 mg to 150 mg calculated as free base.

In some embodiments, in the unit dosage pharmaceutical composition, the mass of compound I or a pharmaceutically acceptable salt thereof is 25 mg to 100 mg calculated as free base.

In some embodiments, in the unit dosage pharmaceutical composition, the mass of compound I or a pharmaceutically acceptable salt thereof is 10 mg calculated as free base.

In some embodiments, in the unit dosage pharmaceutical composition, the mass of compound I or a pharmaceutically acceptable salt thereof is 25 mg calculated as free base.

In some embodiments, in the unit dosage pharmaceutical composition, the mass of compound I or a pharmaceutically acceptable salt thereof is 50 mg calculated as free base.

In some embodiments, in the unit dosage pharmaceutical composition, the mass of compound I or a pharmaceutically acceptable salt thereof is 75 mg calculated as free base.

In some embodiments, in the unit dosage pharmaceutical composition, the mass of compound I or a pharmaceutically acceptable salt thereof is 100 mg calculated as free base.

In some embodiments, in the unit dosage pharmaceutical composition, the mass of compound I or a pharmaceutically acceptable salt thereof is 150 mg calculated as free base.

In some embodiments, in the unit dosage pharmaceutical composition, the mass of compound I or a pharmaceutically acceptable salt thereof is 200 mg calculated as free base.

In some embodiments, in the unit dosage pharmaceutical composition, the mass of compound I or a pharmaceutically acceptable salt thereof is 400 mg calculated as free base.

In some embodiments, calculated as free base, the mass of compound I or the pharmaceutically acceptable salt thereof is 0.1-99.9% of the total mass of the pharmaceutical composition, preferably 5-90%, and more preferably 25-65%.

In some embodiments, the unit dosage pharmaceutical composition further comprises one or more pharmaceutically acceptable carriers such as an excipient, a disintegrant, a lubricant, etc. and the mass percentage of the pharmaceutically acceptable carriers is 0.1-99.9%, preferably 10-95%, and more preferably 35-75%.

In some embodiments, the unit dosage pharmaceutical composition is a pharmaceutical preparation suitable for oral administration.

In some embodiments, the unit dosage pharmaceutical composition is a liquid preparation or a solid preparation.

In some typical embodiments, the unit dosage pharmaceutical composition is an oral solid preparation, and preferably a tablet or a capsule.

In a case that the unit dosage pharmaceutical composition is a capsule, the pharmaceutically acceptable carriers are preferably selected from a filler and a lubricant, An exemplary filler is calcium hydrogen phosphate dihydrate, and an exemplary lubricant is glyceryl behenate.

In another aspect, the present application also provides the unit dosage pharmaceutical composition comprising compound I-0 or a pharmaceutically acceptable salt thereof of the present application for use as a medicament.

In another aspect, the present application also provides the unit dosage pharmaceutical composition comprising compound I or a pharmaceutically acceptable salt thereof of the present application for use as a medicament.

In another aspect, the present application also provides use of the unit dosage pharmaceutical composition including compound I-0 or a pharmaceutically acceptable salt thereof, or the unit dosage pharmaceutical composition comprising compound I or a pharmaceutically acceptable salt thereof of the present application in the preparation of a medicament for preventing and/or treating an AKT protein kinase-mediated disease or disease state.

In another aspect, the present application also provides use of the unit dosage pharmaceutical composition including compound I-0 or a pharmaceutically acceptable salt thereof, or the unit dosage pharmaceutical composition comprising compound I or a pharmaceutically acceptable salt thereof of the present application in the prevention and/or treatment of an AKT protein kinase-mediated disease or disease state.

In another aspect, the present application also provides a method for preventing and/or treating an AKT protein kinase-mediated disease or disease state, wherein the method comprises administering the unit dosage pharmaceutical composition comprising compound I-0 or a pharmaceutically acceptable salt thereof, or the unit dosage pharmaceutical composition comprising compound I or a pharmaceutically acceptable salt thereof of the present application to the subject in need.

In another aspect, the present application also provides the unit dosage pharmaceutical composition comprising compound I-0 or a pharmaceutically acceptable salt thereof, or the unit dosage pharmaceutical composition comprising compound I or a pharmaceutically acceptable salt thereof of the present application that is used for preventing and/or treating an AKT protein kinase-mediated disease or disease state.

In some embodiments, the AKT protein kinase-mediated disease or disease state is cancer.

In some typical embodiments, the cancer is breast cancer, prostate cancer or ovarian cancer.

In some typical embodiments, the cancer is prostate cancer.

Relevant Definitions

Unless otherwise specified, the following terms used in the description and claims have the following meanings.

Compound I-0 of the present application includes its tautomer. A tautomer results from the exchange of a single bond and an adjacent double bond and transfer of the two bonds together with a proton. Exemplarily, compound

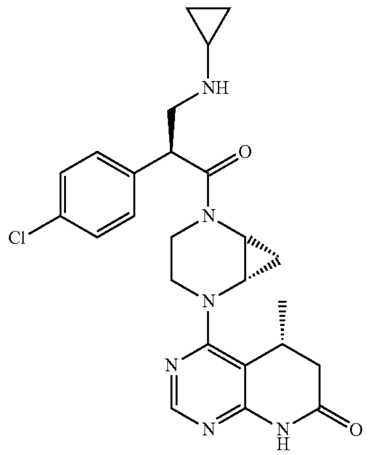

is taken as an example, which may be transformed into

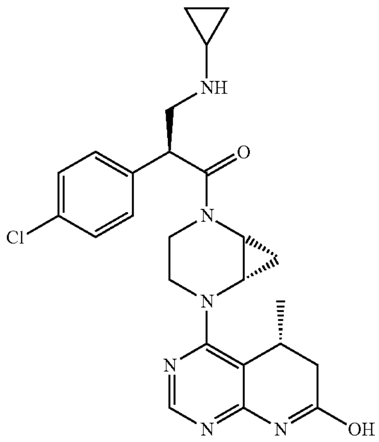

under certain conditions, and compound

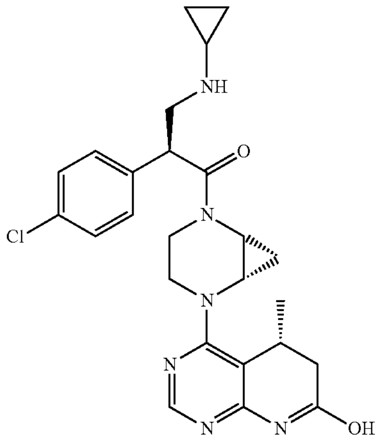

is a tautomer of compound

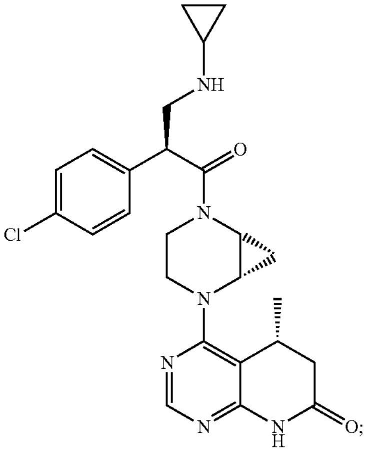

correspondingly, tautomers of other compounds in compound I-0 shall also fall within the protection extent of the present application.

The compounds or the pharmaceutically acceptable salts thereof of the present application include their hydrates. Specifically, the compounds or the pharmaceutically acceptable salts thereof of the present application include hydrates of the compounds and hydrates of the pharmaceutically acceptable salts of the compounds.

A numerical range in the present application refers to each integer within the given range. For example, "C1-C4" refers to that the group may have 1 carbon atom, 2 carbon atoms, 3 carbon atoms or 4 carbon atoms; and "C3-C6" refers to that the group may have 3 carbon atoms, 4 carbon atoms, 5 carbon atoms or 6 carbon atoms.

The term "alkyl" refers to saturated aliphatic hydrocarbyl groups, including straight chain or branched saturated hydrocarbyl that has the indicated number of carbon atoms. For example, the term "C1-C4 alkyl" includes C1 alkyl, C2 alkyl, C3 alkyl or C4 alkyl. Examples of C1-C4 alkyl include, but not limited to, methyl, ethyl, n-propyl, isopropyl, n-butyl, isobutyl, tert-butyl.

The term "cycloalkyl" refers to monocyclic saturated hydrocarbon systems without heteroatoms and double bonds. Examples of the term "C3-C6 cycloalkyl" include, but are not limited to, cyclopropyl, cyclobutyl, cyclopentyl, and cyclohexyl.

The term "unit dosage" refers to a specific form of product that exists individually and relatively independently in a kit or pharmaceutical packaging, which includes a certain amount of active ingredient. Exemplarily, the "unit dosage" of the present application may be understood as a tablet or capsule of oral solid preparation, and according to the common oral solid preparation, the weight of said tablet or capsule of drug may be any weight appropriate in the art, such as from 100 mg to 1500 mg. In other examples, the "unit dosage" of the present application may be understood as an oral liquid preparation such as a bottle of oral liquid or a capsule containing liquid, and according to the common oral liquid or capsule, the volume of the liquid in said bottle or capsule may be any appropriate volume in the art, such as from 20 μL to 10 mL, etc.

The term "pharmaceutically acceptable salt" refers to a salt that retains the biological efficacy of free acid and base in a specific compound and does not cause adverse biological effects. For example, the pharmaceutically acceptable salt may be an acid (including organic acids and inorganic acids) addition salt or a base (including organic bases and inorganic bases) addition salt.

The pharmaceutically acceptable salt of the present application can be synthesized from a parent compound containing acid radicals or base groups by the conventional chemical method. In general, a preparation method of the salt includes the following steps: in water or an organic solvent or a mixture of the two, reacting a compound in the form of free acid or base with appropriate stoichiometric base or acid to prepare a salt.

The term "pharmaceutically acceptable carrier" refers to a carrier that has no obvious stimulating effect on the body and will not impair the biological activity and performance of an active compound. Pharmaceutically acceptable carriers include, but are not limited to, any diluent, disintegrant, adhesive, glidant, and wetting agent that have been approved by the National Medical Products Administration for human or animal use.

Unless otherwise specified, the abbreviations in the present application have the following meanings:

M: mol/L
mM: mmol/L
nM: nmol/L
Boc: tert-butoxycarbonyl
DCM: dichloromethane
DEA: diethylamine
DIEA: N,N-diisopropylethylamine
HATU: 2-(7-azabenzotriazol)-N,N,N',N'-tetramethyluronium hexafluorophosphate
RT: retention time
SFC: supercritical fluid chromatography
h: hour
min: minute
TK: tyrosine kinase
SEB: fluorescent signal enhancer
HTRF: homogeneous time resolved fluorescence
DTT: dithiothreitol
QD: once a day
po: oral administration
TV: tumor volume
PG: 1,2-propanediol
T/C: relative tumor proliferation rate
TGI: tumor growth inhibition rate

BRIEF DESCRIPTION OF THE DRAWINGS

In order to more clearly describe the technical solutions of the examples of the present application and the prior art, the drawings that need to be used in the examples and the prior art will be briefly introduced below. Obviously, the drawings in the following description are some embodiments of the present application only, and those skilled in the art may also obtain other drawings according to these drawings.

DETAILED DESCRIPTION OF THE EMBODIMENTS

Figure 1:
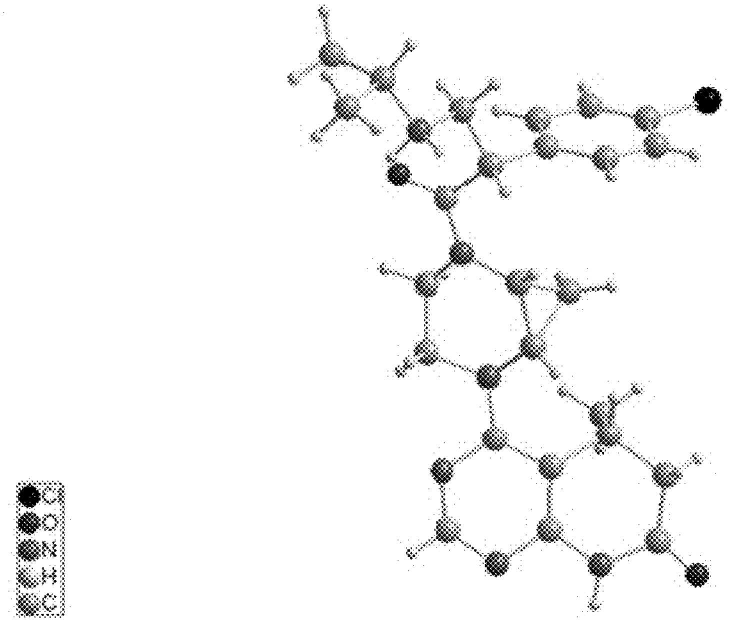
FIG. 1 is a schematic diagram of a single molecule of isomer 2 of Example 1.

The pharmaceutical compositions of the present application, the preparation methods and application thereof, including the preparation methods of the compounds, will be more specifically described below. However, these specific descriptions are not intended to limit the present application in any manner.

Preparation Examples

Preparation Example 1 Preparation of (R)-4-chloro-5-methyl-5,8-dihydropyrido[2,3-d]pyrimidin-7 (6H)-one

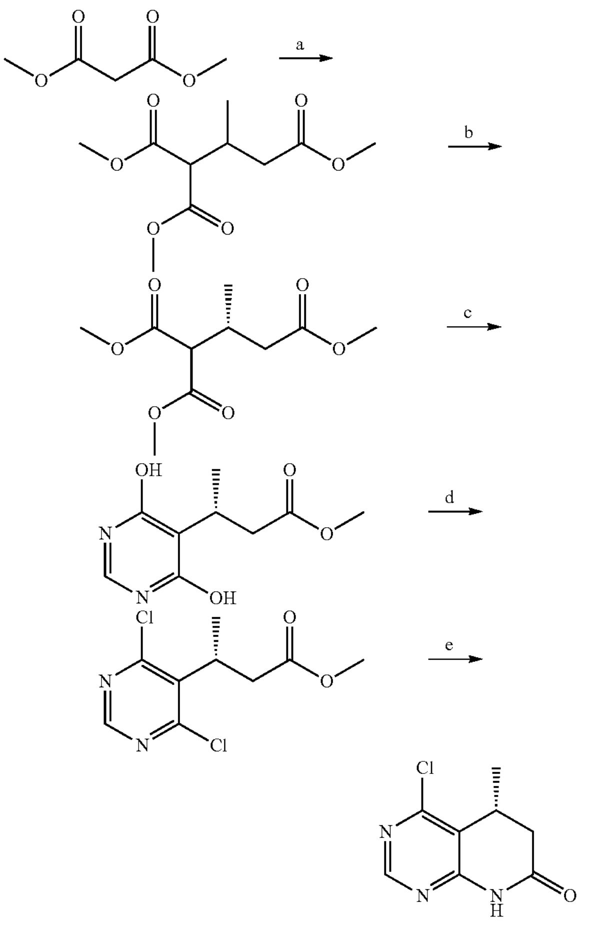

a) Trimethyl 2-methylpropane-1,1,3-tricarboxylate

Under the protection of nitrogen gas, a sodium methylate-methanol solution (30 wt %, 50.32 g) was added to methanol (900 mL) at 20° C., the mixture was heated to 70° C., dimethyl malonate (461.12 g) and ethyl crotonate (349.46 g) were mixed until uniform and dropwise added to the above sodium methylate-methanol solution, and the reaction solution reacted at 70° C. for 3 h. After the reaction was completed, the reaction solution was evaporated under reduced pressure to remove the solvent, ethyl acetate (1 L) was added, the mixture was regulated with 4 M hydrochloric acid until the pH of the mixture was 7-8, water (500 mL) was added, the solution was separated and evaporated under reduced pressure to remove the organic phase so as to yield a yellow liquid (777.68 g). 1H NMR (400 MHz, DMSO-$d_6$) δ (ppm) 3.67 (s, 3H), 3.65 (s, 3H), 3.59 (s, 3H), 3.56 (d, J=6.8 Hz, 1H), 2.45-2.58 (m, 2H), 2.23-2.29 (m, 1H), 0.93 (d, J=6.8 Hz, 3H).

b) Trimethyl (R)-2-methylpropane-1,1,3-tricarboxylate

Disodium hydrogen phosphate (4.5 g) was dissolved in deionized water (1.5 L) at 25° C., the solution was regulated with 2 N hydrochloric acid until the pH of the solution was 7.05, trimethyl 2-methylpropane-1,1,3-tricarboxylate (150.46 g) and lipase (*Candida rugosa,* 40 g, added in 6 d) were added, the mixture was regulated with a 2 N sodium hydroxide solution until the pH of the mixture was 7.0-7.6, and the reaction solution reacted at 35° C. for 6 d. Chirality detection ee %>98%, and chirality detection conditions: Chiralpak IC, 4.6×250 mm, 5 μm, and n-hexane: ethanol=9:1 (volume ratio). The reaction solution was cooled to 10° C. and regulated with 3 M hydrochloric acid until the pH of the reaction solution was 3-4, ethyl acetate (500 mL) was added, the mixture was subjected to suction filtration, an obtained filter cake was washed with ethyl acetate (600 mL), the solution was separated, a saturated sodium bicarbonate aqueous solution (100 mL) was added for washing, the solution was separated, and an obtained organic phase was concentrated to yield a pale-yellow liquid (26.89 g). $^1$H NMR (400 MHz, $CDCl_3$) δ (ppm) 3.74 (s, 6H), 3.68 (s, 3H), 3.46 (d, J=7.2 Hz, 1H), 2.71-2.79 (m, 1H), 2.54 (dd, J=15.6, 4.8 Hz, 1H), 2.32 (dd, J=16.0, 8.4 Hz, 1H), 1.06 (d, J=6.8 Hz, 3H).

c) Methyl (R)-3-(4,6-dihydroxypyrimidin-5-yl)butanoate

Under the protection of nitrogen gas, formamidine acetate (11.33 g) was dissolved in methanol (200 mL) at 20° C., the solution was cooled to 0° C., a sodium methylate-methanol solution (30 wt %, 55.62 g) was dropwise added, the reaction solution reacted at 0° C. for 60 min, a methanol (60 mL) solution of trimethyl (R)-2-methylpropane-1,1,3-tricarboxylate (24.07 g) was dropwise added, and the reaction solution was naturally heated to 20° C. and reacted for 10 h. After the reaction was completed, the reaction solution was cooled to 0° C., regulated with 3 N hydrochloric acid until the pH of the reaction solution was 5-6, evaporated under reduced pressure to remove the solvent, cooled to 0° C., and regulated with 3 N hydrochloric acid until the pH of the reaction solution was 3, after a solid was precipitated, the reaction solution was subjected to suction filtration to collect the solid, and an obtained filter cake was washed with ice water (100 mL) and dried in vacuum to yield a white solid (18.79 g) that was directly used at the next step.

d) Methyl (R)-3-(4,6-dichloropyrimidin-5-yl)butanoate

Under the protection of nitrogen gas, methyl (R)-3-(4,6-dihydroxypyrimidin-5-yl)butanoate (14.63 g) was dispersed into acetonitrile (70 mL) at 22° C., phosphorus oxychloride (26.42 g) and diisopropylethylamine (12.51 g) were dropwise added in sequence, the system released heat obviously and was heated to 60° C., the solids were gradually fully dissolved, and the reaction solution reacted for 18 h. After the reaction was completed, the reaction solution was cooled to 0° C., ethyl acetate (100 mL) was added, the mixture was regulated with a saturated sodium bicarbonate solution until the pH of the mixture was 7-8, extracted with ethyl acetate (50 mL×3), and evaporated under reduced pressure to remove the organic phase so as to yield a yellow solid (13.89 g) that was directly used at the next step.

e)(R)-4-chloro-5-methyl-5,8-dihydropyrido[2,3-d]pyrimidin-7 (6H)-one

Methyl (R)-3-(4,6-dichloropyrimidin-5-yl)butanoate (13.89 g) and ammonia water (25-28 wt %, 70 mL) were placed in a 100 mL high-pressure kettle at 20° C., and the reaction solution was heated to 50° C. and reacted for 18 h. After the reaction was completed, the reaction solution was cooled to 0° C. and subjected to suction filtration, and an obtained filter cake was beaten with a mixture (30 mL) of petroleum ether and ethyl acetate in a volume ratio of 10:1 to yield a pale-yellow solid (7.32 g). LC-MS (ESI) m/z: 198 (M+H). $^1$H NMR (300 MHz, $CDCl_3$) δ (ppm) 1.30 (d, J=7.2 Hz, 3H), 2.65-2.69 (m, 1H), 2.86-2.92 (m, 1H), 3.47-3.54 (m, 1H), 8.64 (s, 1H), 10.10 (s, 1H).

Example 1 Preparation of (R)-4-((1S,6R)-5-((S)-2-(4-chlorophenyl)-3-(isopropylamino)propionyl)-2,5-diazabicyclo[4.1.0]heptan-2-yl)-5-methyl-5,8-dihydropyrido[2,3-d]pyrimidin-7 (6H)-one

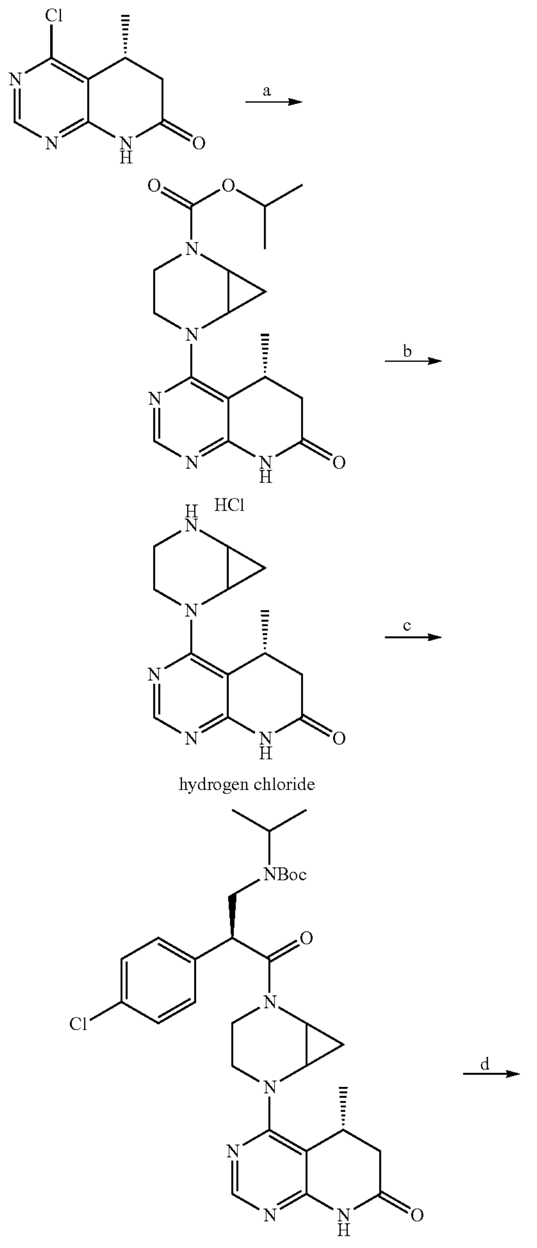

-continued

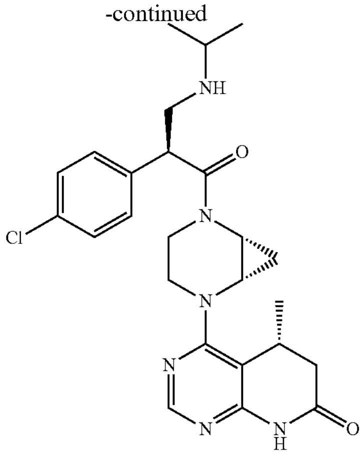

and

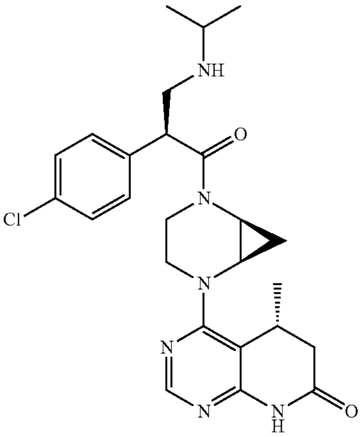

Reaction conditions: a) 2,5-diazabicyclo[4.1.0]heptane-2-carboxylate, N-tert-butyl methylpyrrolidone, and 4-dimethylaminopyridine; b) hydrogen chloride/1,4-dioxane (4.0 M) and dichloromethane; c)(S)-3-((tert-butoxycarbonyl)(isopropyl)amino)-2-(4-chlorophenyl)-propionic acid, 2-(7-benzotriazole oxide)-N,N,N',N'-tetramethyluronium hexafluorophosphate, 4-dimethylaminopyridine, and N,N-dimethylformamide; d) trifluoroacetic acid and dichloromethane.

a) Tert-butyl 5-((R)-5-methyl-7-oxo-5,6,7,8-tetrahydropyrido[2,3-d]pyrimidin-4-yl)-2,5-diazabicyclo[4.1.0]heptane-2-carboxylate Under the protection of nitrogen gas, (R)-4-chloro-5-methyl-5,8-dihydropyrido[2,3-d]pyrimidin-7 (6H)-one (0.21 g), tert-butyl 2,5-diazabicyclo[4.1.0]heptane-2-carboxylate (0.31 g), and 4-dimethylaminopyridine (0.39 g) were dissolved in N-methylpyrrolidone (5 mL) at 22° C., and the reaction solution was heated to 140° C. and reacted for 3 h. After the reaction was completed, the reaction solution was cooled to 20° C., poured into ice water (20 mL), extracted with ethyl acetate (20 mL×2), washed with a saturated salt solution (10 mL×3), evaporated under reduced pressure to remove the solvent, and separated by silica gel column chromatography (petroleum ether:ethyl acetate=(3:1)-(1:1)) to yield a pale-yellow liquid (0.28 g). LC-MS (ESI) m/z: 360 (M+H).

b)(5R)-4-(2,5-diazabicyclo[4.1.0]heptan-2-yl)-5-methyl-5,8-dihydropyrido[2,3-d]pyrimidin-7 (6H)-one hydrochloride Tert-butyl 5-((R)-5-methyl-7-oxo-5,6,7,8-tetrahydropyrido[2,3-d]pyrimidin-4-yl)-2,5-diazabicyclo[4.1.0]heptane-2-carboxylate (0.28 g) was dissolved in dichloromethane (5 mL) at 20° C., hydrogen chloride/1,4-dioxane (4.0 mL) was added, and the reaction solution reacted for 1 h. After the reaction was completed, the reaction solution was evaporated under reduced pressure to remove the solvent so as to yield a yellow solid (0.23 g) that was directly used at the next step. c) Tert-butyl (2S)-2-(4-chlorophenyl)-3-(5-((R)-5-methyl-7-oxo-5,6,7,8-tetrahydropyrido[2,3-d]pyrimidin-4-yl)-2,5-diazabicyclo[4.1.0]heptan-2-yl)-3-oxopropyl)(isopropyl)carbamate Under the protection of nitrogen gas, (5R)-4-(2,5-diazabicyclo[4.1.0]heptan-2-yl)-5-methyl-5,8-dihydropyrido[2,3-d]pyrimidin-7 (6H)-one hydrochloride (0.20 g) and(S)-3-((tert-butoxycarbonyl)(isopropyl)amino)-2-(4-chlorophenyl)-propionic acid (0.22 g) were dissolved in N,N-dimethylformamide (5 mL) at 20° C., 2-(7-benzotriazole oxide)-N,N,N',N'-tetramethyluronium hexafluorophosphate (0.59 g) and 4-dimethylaminopyridine (0.48 g) were added, and the reaction solution reacted at 25° C. for 4 h. After the reaction was completed, water (20 mL) was added to the reaction solution, the mixture was extracted with ethyl acetate (10 mL×3), an obtained organic phase was washed with a saturated salt solution (10 mL×2), and the solution was evaporated under reduced pressure to remove the organic phase and separated by column chromatography (dichloromethane:methanol=50:1) to yield a yellow solid (0.18 g). LC-MS (ESI) m/z: 583 (M+H).

d)(R)-4-((1S,6R)-5-((S)-2-(4-chlorophenyl)-3-(isopropylamino)propionyl)-2,5-diazabicyclo[4.1.0]heptan-2-yl)-5-methyl-5,8-dihydropyrido[2,3-d]pyrimidin-7 (6H)-one Tert-butyl (2S)-2-(4-chlorophenyl)-3-(5-((R)-5-methyl-7-oxo-5,6,7,8-tetrahydropyrido[2,3-d]pyrimidin-4-yl)-2,5-diazabicyclo[4.1.0]heptan-2-yl)-3-oxopropyl)(isopropyl)carbamate (0.18 g) was dissolved in dichloromethane (2 mL) at 20° C., trifluoroacetic acid (0.86 mL) was added, and the reaction solution reacted for 3 h. After the reaction was completed, dichloromethane (10 mL) was added to the reaction solution, a 2 M sodium hydroxide solution was dropwise added at 0° C. to regulate the pH of the mixture to 12, the solution was separated, an obtained organic phase was washed with a saturated salt solution (5 mL), and the solution was dried with anhydrous sodium sulfate and evaporated under reduced pressure to remove the organic phase so as to yield a yellow solid (0.10 g). The yellow solid was resolved by preparative high-performance liquid chromatography to yield isomer 1 (3 mg) and isomer 2 (12 mg). Preparative high-performance liquid chromatography conditions: chromatographic column: Aglient 5 μm prep-C18 50×21.2 mm; mobile phase A: water (containing 0.1 vol % of ammonium water (25-28 wt %)); and mobile phase B: methanol. Gradient: time: 0-10 min, 60-70% (volume percentage) of B phase.

Isomer 1: $RT_1$=5.3 min; LC-MS (ESI) m/z: 483 (M+H).

Isomer 2: RT-5.9 min; LC-MS (ESI) m/z: 483 (M+H); $^1H$ NMR (400 MHz, $CDCl_3$) δ (ppm) 8.27 (d, J=7.6 Hz, 1H), 7.92 (s, 1H), 7.27-7.30 (m, 4H), 4.23-4.29 (m, 1H), 3.90-3.95 (m, 1H), 3.81-3.85 (m, 1H), 3.69-3.72 (m, 1H), 3.44-3.59 (m, 1H), 3.20-3.38 (m, 3H), 3.01-3.05 (m, 1H), 2.70-2.85 (m, 3H), 2.47-2.57 (m, 1H), 2.21-2.25 (m, 1H), 1.25-1.28 (m, 3H), 1.03-1.11 (m, 6H), 0.82-0.90 (m, 2H).

Configurations were determined by single crystal diffraction, and it was determined that isomer 2 was the title compound of the present example:

Preparation of a single crystal: isomer 2 (30.0 mg) and isopropanol (2.0 mL) were placed in a 5 mL screw flask and stirred for 5 min until the solid was fully dissolved. Oxalic acid dihydrate (3.9 mg) was weighed and placed in the above flask, a white solid was gradually precipitated in the flask, the reaction solution was stirred at the room temperature for 3 h, and a large amount of white solid was precipitated in the flask. Methanol (1.0 mL) was placed in the flask, the white solid gradually disappeared, and after becoming clear, the solution was stirred for 1 h. The solution was filtered with a 0.22 μm microfiltration membrane to a 3 mL screw flask, and the opening of the flask was covered with a plastic wrap. The plastic warp covering the opening of the flask was pierced by using a needle to form 8 small holes, the flask was placed at the room temperature for 7 d, and an oxalate single crystal of isomer 2 was obtained.

Single Crystal Diffraction Experiment:

Single crystal X-ray diffractometer: BRUKER D8 VENTURE PHOTON II

Wavelength: Ga Kα (λ=1.34139 Å)

Test temperature: 190 K

Computer program for structural analysis: SHELXL-2018

Single crystal data: molecular formula: $C_{55}H_{72}Cl_2N_{12}O_9$; molecular weight: 1116.14; crystal system: hexagonal crystal system; space group: P61; cell parameters of the crystal: a=25.8406(15) Å, b=25.8406 (15) Å, c=45.916 (3) Å, α=90°, β=90°, and γ=120°; unit cell volume: V=26552 (4) Å3; the number of molecular formulas contained in the unit cell: Z=12; calculated density: $D_{calc}$=0.838 g/$cm^3$; $R(F_o)$: 0.0730; $R_w(F_o^2)$: 0.2069; goodness of fit(S): 1.034; and Flack parameter: 0.066 (9).

Figure 2:
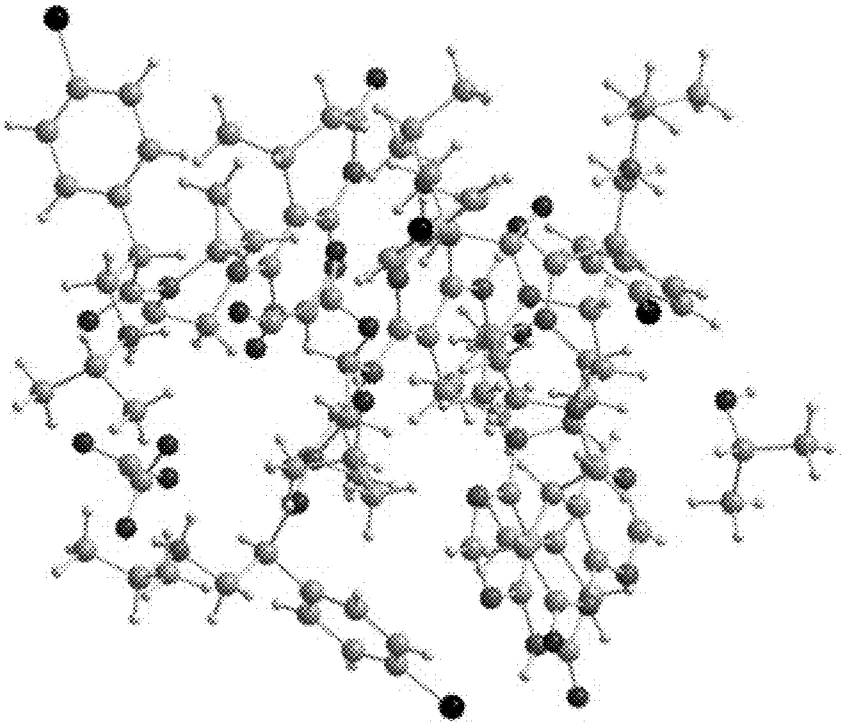
FIG. 2 is a schematic diagram of asymmetric structural unit of an oxalate single crystal of isomer 2 of Example 1.

Structural description: single crystal X-ray diffraction and structural analysis show that the prepared single crystal is an oxalate isopropanol complex of isomer 2. Asymmetric structural unit of the crystal include four isomer 2 molecules, two oxalic acid molecules, and two isopropanol molecules, wherein isomer 2 and oxalic acid forms an oxalate. The single molecule of isomer 2 is shown in FIG. 1, and the asymmetric structural unit of the oxalate single crystal is shown in FIG. 2. The structural formula is shown below:

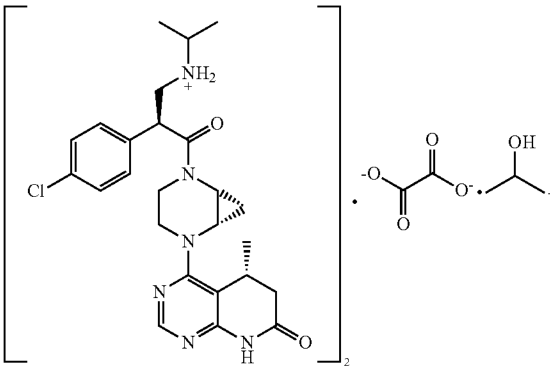

Example 2 Preparation of (R)-4-((1S,6R)-5-((S)-2-(4-chlorophenyl)-3 (cyclopropylamino)propionyl)-2,5-diazabicyclo[4.1.0]heptan-2-yl)-5-methyl-5,8-dihydropyrido[2,3-d]pyrimidin-7 (6H)-one
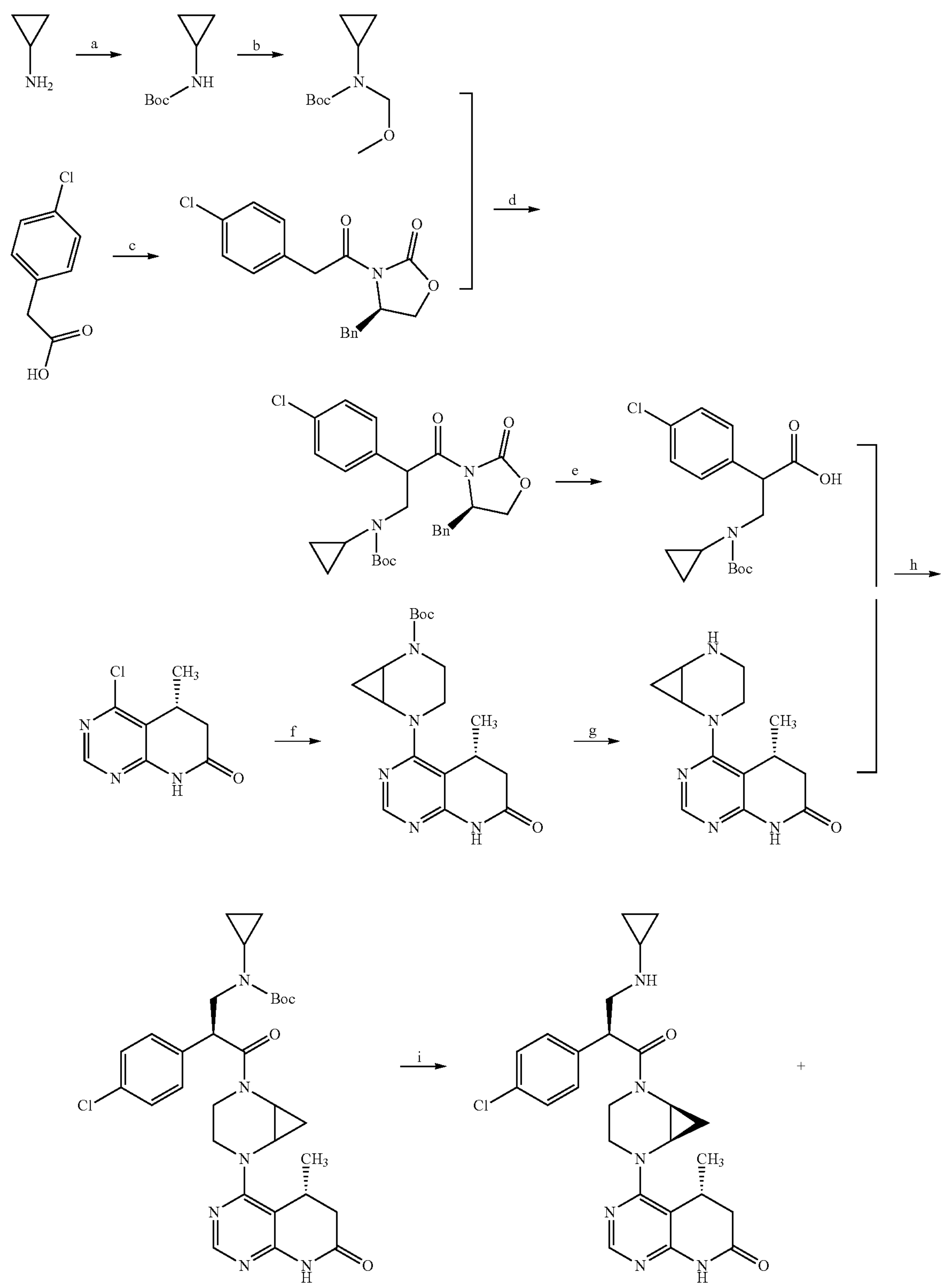
isomer 1

-continued

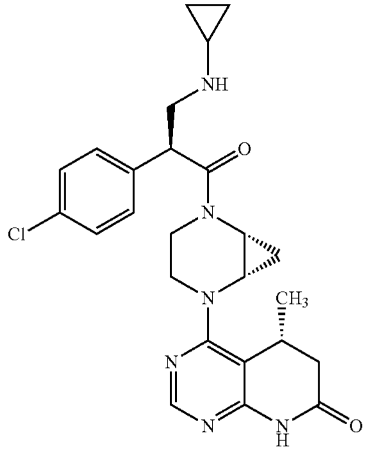

isomer 2

Reaction conditions: a) triethylamine, di-tert-butyl dicarbonate, and dichloromethane; b) sodium bis(trimethylsilyl) amide (2.0 mol/L tetrahydrofuran solution), bromomethyl methyl ether, and 2-methyltetrahydrofuran; c)(R)-4-benzyloxazolidin-2-one, diisopropylethylamine, trimethylacetyl chloride, and toluene; d) titanium tetrachloride (1 mol/L toluene solution), diisopropylethylamine, and dichloromethane; e) hydrogen peroxide solution (30 wt %), lithium hydroxide monohydrate, tetrahydrofuran, and water; f) tert-butyl 2,5-diazabicyclo[4.1.0]heptane-2-carboxylate, 4-dimethylaminopyridine, and N-methylpyrrolidone; g) hydrogen chloride/dioxane (4.0 M); h) 2-(7-benzotriazole oxide)-N, N,N',N'-tetramethyluronium hexafluorophosphate, diisopropylethylamine, and N,N-dimethylformamide; and i) hydrogen chloride/dioxane (4.0 M).

a) Tert-butyl cyclopropylcarbamate

Under the protection of nitrogen gas, cyclopropylamine (9.3 g) and triethylamine (19.7 g) were dissolved in dichloromethane (100 mL) at 20° C., di-tert-butyl dicarbonate (35.48 g) was dropwise added at 0° C., the reaction solution reacted at 20° C. for 16 h, and after the reaction was completed, the reaction solution was desolvated to yield a colorless liquid (24.3 g). $^1$H NMR (400 MHz, $CDCl_3$) δ (ppm) 0.47-0.50 (m, 2H), 0.66-0.72 (m, 2H), 1.44 (s, 9H), 2.53 (m, 1H), 4.79 (s, 1H).

b) Tert-butyl cyclopropyl(methoxymethyl)carbamate

Under the protection of nitrogen gas, tert-butyl cyclopropylcarbamate (24.3 g) was dissolved in 2-methyltetrahydrofuran (100 mL), sodium bis(trimethylsilyl)amide (120 mL) was dropwise added at 0° C., the reaction solution was stirred at 0° C. for 1 h, bromomethyl methyl ether (35.7 g) was dropwise added at 0° C., and the reaction solution was stirred at 0° C. for 6 h, poured into ice water (50 g), separated, extracted with ethyl acetate (100 mL×2), and directly concentrated to yield a colorless liquid (29.1 g) that was not purified and directly used at the next step.

c)(R)-4-benzyl-3-(2-(4-(chlorophenyl) acetyl) oxazolidin-2-one

Under the protection of nitrogen gas, 2-(4-chlorophenyl) acetic acid (50 g), (R)-4-benzyloxazolidin-2-one (45.5 g), and diisopropylethylamine (127.3 g) were dissolved in toluene (600 mL), trimethylacetyl chloride (38.4 g) was dropwise added at 15° C., the reaction solution was refluxed and stirred for 16 h, poured into water (200 mL), separated, and washed with a saturated salt solution (120 mL), and an obtained organic phase was dried and concentrated to yield a crude product. The crude product was separated and purified by column chromatography (PE: EA=5:1) to yield a white solid (32 g). $^1$H NMR (400 MHz, DMSO-$d_6$) δ (ppm) 2.88-3.02 (m, 2H), 4.12-4.37 (m, 4H), 4.64-4.70 (m, 1H), 7.13-7.16 (m, 2H), 7.23-7.32 (m, 5H), 7.39-7.42 (m, 2H).

d) Tert-butyl ((S)-3-((R)-4-benzyl-2-oxazolidin-3-yl)-2-(4-chlorophenyl)-3-oxopropyl)(cyclopropyl)carbamate Under the protection of nitrogen gas, (R)-4-benzyl-3-(2-(4-(chlorophenyl) acetyl) oxazolidin-2-one (3.48 g) was dissolved in dichloromethane (60 mL), a titanium tetrachloride-toluene solution (13 mL) was dropwise added at 0° C., the reaction solution was stirred at 0° C. for 2 h, DIPEA (1.49 g) was dropwise added, the reaction solution was stirred at 0° C. for 1.5 h, tert-butyl cyclopropyl(methoxymethyl)carbamate (2.77 g) was dropwise added, the reaction solution was stirred at 0° C. for 6 h. After the reaction was completed, the reaction solution was poured into a saturated ammonium chloride solution (30 mL), separated, and washed with a saturated salt solution (120 mL), and an obtained organic phase was dried and concentrated to yield a crude product. The crude product was separated and purified by silica gel column chromatography (PE: EA=10: 1) to yield a colorless oily product (2.50 g).

e)(S)-3-((tert-butoxycarbonyl)(cyclopropyl)amino)-2-(4-chlorophenyl) propanoic acid Lithium hydroxide monohydrate (0.63 g) was dissolved in water (18 mL), tetrahydrofuran (20 mL) was added, hydrogen peroxide (1.6 mL) was dropwise added at 0° C., tert-butyl ((S)-3-((R)-4-benzyl-2-oxazolidin-3-yl)-2-(4-chlorophenyl)-3-oxopropyl)(cyclopropyl)carbamate (2.50 g) was added at 0° C., the reaction solution was stirred at 0° C. for 3 h, a saturated sodium sulfite solution (15 mL) was added to the reaction solution, the reaction solution reacted for 1.5 h, was regulated with a saturated potassium bisulfate solution until the pH of the reaction solution was 3-4, extracted with ethyl acetate (30 mL×2), and separated, and an obtained organic phase was dried and concentrated to yield a crude product. The crude product was separated and purified by column chromatography (PE:EA=1:1) to yield a colorless solid (1.26 g). $^1H$ NMR (400 MHz, DMSO-$d_6$) δ (ppm): 0.45-0.48 (m, 2H), 0.60-0.64 (m, 2H), 1.30 (s, 9H), 2.19 (s, 1H), 3.61 (d, J-7.6 Hz, 1H), 3.95 (t, J=8.0 Hz, 1H), 7.37 (dd, J=26.8, 8.8 Hz, 4H), 12.7 (s, 1H).

f) 5-((R)-5-methyl-7-oxo-5,6,7,8-tetrahydropyrido[2,3-d]pyrimidin-4-yl)-2,5-diazabicyclo[4.1.0]heptane-2-carboxylate Under the protection of nitrogen gas, (R)-4-chloro-5-methyl-5,8-dihydropyrido[2,3-d]pyrimidin-7 (6H)-one (300 mg), tert-butyl 2,5-diazabicyclo[4.1.0]heptane-2-carboxylate (455 mg), and 4-dimethylaminopyridine (600 mg) were dissolved in N-methylpyrrolidone (5 mL), the reaction solution was stirred at 120° C. for 12 h, poured into water (50 mL), extracted with ethyl acetate (20 mL×2), and washed with a saturated salt solution (15 mL), an obtained organic phase was dried and desolvated to yield a crude product. The crude product was separated and purified by silica gel column chromatography (PE:EA=(1:1)-(1:2)) to yield a yellow solid (400 mg).

g)(5R)-4-(2,5-diazabicyclo[4.1.0]heptan-2-yl)-5-methyl-5,8-dihydropyrido[2,3-d]pyrimidin-7 (6H)-one 5-((R)-5-methyl-7-oxo-5,6,7,8-tetrahydropyrido[2,3-d]pyrimidin-4-yl)-2,5-diazabicyclo[4.1.0]heptane-2-carboxylate (400 mg) was dissolved in dioxane (5 mL), a hydrogen chloride-dioxane solution (5 mL) was dropwise added, the reaction solution was stirred at 25° C. for 2 h, and after the reaction was completed, the reaction solution was directly concentrated to yield a yellow crude solid that was directly used at the next step.

h) Tert-butyl ((S)-2-(4-chlorophenyl)-3-((1R,6S)-5-((R)-5-methyl-7-oxo-5,6,7,8-tetrahydropyrido[2,3-d]pyrimidin-4-yl)-2,5-diazabicyclo[4.1.0]heptan-2-yl)-3-oxopropyl)(cyclopropyl)carbamate Under the protection of nitrogen gas, (5R)-4-(2,5-diazabicyclo[4.1.0]heptan-2-yl)-5-methyl-5,8-dihydropyrido[2,3-d]pyrimidin-7 (6H)-one (270 mg), the product obtained at step e)(389 mg), 2-(7-benzotriazole oxide)-N,N,N',N'-tetramethyluronium hexafluorophosphate (474 mg), and diisopropylethylamine (671 mg) were dissolved in N,N-dimethylformamide (10 mL), the reaction solution was stirred at 25° C. for 3 h. After the reaction was completed, the reaction solution was poured into water (50 mL), extracted with ethyl acetate (20 mL×2), and washed with a saturated salt solution (10 mL×3), and an obtained organic phase was dried and concentrated to yield a crude product. The crude product was separated and purified by column chromatography (PE:EA=1:2) to yield a yellow solid (320 mg).

i)(R)-4-((1S,6R)-5-((S)-2-(4-chlorophenyl)-3 (cyclopropylamino)propionyl)-2,5-diazabicyclo[4.1.0]heptan-2-yl)-5-methyl-5,8-dihydropyrido[2,3-d]pyrimidin-7 (6H)-one Tert-butyl ((S)-2-(4-chlorophenyl)-3-((1R,6S)-5-((R)-5-methyl-7-oxo-5,6,7,8-tetrahydropyridyl[2,3-d]pyrimidin-4-yl)-2,5-diazabicyclo[4.1.0]heptan-2-yl)-3-oxopropyl)(cyclopropyl)carbamate (320 mg) was dissolved in dioxane (2.5 mL), hydrogen chloride/dioxane (2.7 mL) was dropwise added, the reaction solution was stirred at 25° C. for 14 h, after the reaction was completed, the reaction solution was concentrated to yield a crude product, and the crude product was regulated with a saturated potassium carbonate solution until the pH of the crude product was 13-14, extracted with DCM (10 mL×2), washed with water (10 mL), desolvated, and resolved by supercritical fluid chromatography to yield isomer 1 (61.2 mg) and isomer 2 (31.2 mg). Configurations were determined by single crystal diffraction, and it was determined that isomer 2 was the title compound of the present example. Resolution instrument and conditions: waters SFC200; chromatographic column: Daicel Chiralcel AS, 250×30 mm I.D., 5 um; mobile phases: A: $CO_2$, B: isopropanol (0.1 vol % of ammonia water (25-28 wt %)), and A: B=70:30 (volume ratio); flow rate: 60 mL/min; and column temperature: 38° C.

Ultra-performance convergence chromatography conditions: chromatographic column: Daicel Chiralcel AD, 2.1×150 mm I.D., 3 um; mobile phase A: $CO_2$; mobile phase B: isopropanol (0.1 vol % of DEA); gradient: time: 0-8 min, 5-40% (volume percentage) of phase B; flow rate: 1 mL/min; and column temperature: 40° C. Isomer 1: RT=3.7 min; and isomer 2: RT=4.6 min. Isomer 1: LC-MS (ESI) m/z: 481 (M+H). $^1H$ NMR (400 MHz, DMSO-$d_6$) δ (ppm): 0.03-0.12 (m, 2H), 0.25-0.30 (m, 2H), 0.66-0.70 (m, 1H), 0.96-1.05 (m, 3H), 1.35-1.40 (m, 1H), 1.93-2.11 (m, 2H), 2.29-2.35 (m, 1H), 2.67-2.77 (m, 2H), 2.80-2.86 (m, 1H), 3.03-3.25 (m, 4H), 3.39-3.48 (m, 1H), 3.69-3.79 (m, 1H), 4.24-4.34 (m, 2H), 7.34-7.41 (m, 4H), 8.17 (s, 1H), 10.52 (s, 1H). Isomer 2: LC-MS (ESI) m/z: 481 (M+H). $^1H$ NMR (400 MHz, DMSO-$d_6$) δ (ppm): 0.14-0.21 (m, 2H), 0.30-0.37 (m, 2H), 0.93-1.07 (m, 4H), 2.03-2.34 (m, 3H), 2.66-2.86 (m, 2H), 3.10-3.25 (m, 4H), 3.36-3.94 (m, 4H), 4.07-4.15 (m, 1H), 4.41-4.45 (m, 1H), 7.32-7.42 (m, 4H), 8.19 (s, 1H), 10.48 (s, 1H).

Example 3 Preparation of(S)-5-((1S,6R)-5-((S)-2-(4-chlorophenyl)-3-(isopropylamino)propionyl)-2,5-diazabicyclo[4.1.0]heptan-2-yl)-4-methyl-1,4-dihydro-2H-pyrimidinyl[4,5-d][1,3]oxazin-2-one

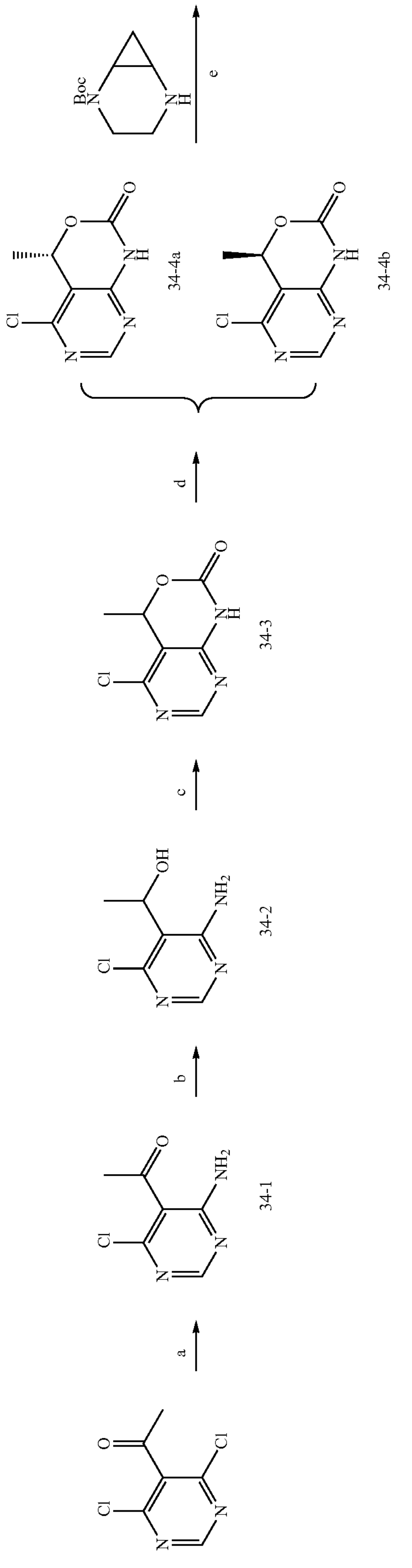
34-1
34-2
34-3
34-4a
34-4b

-continued
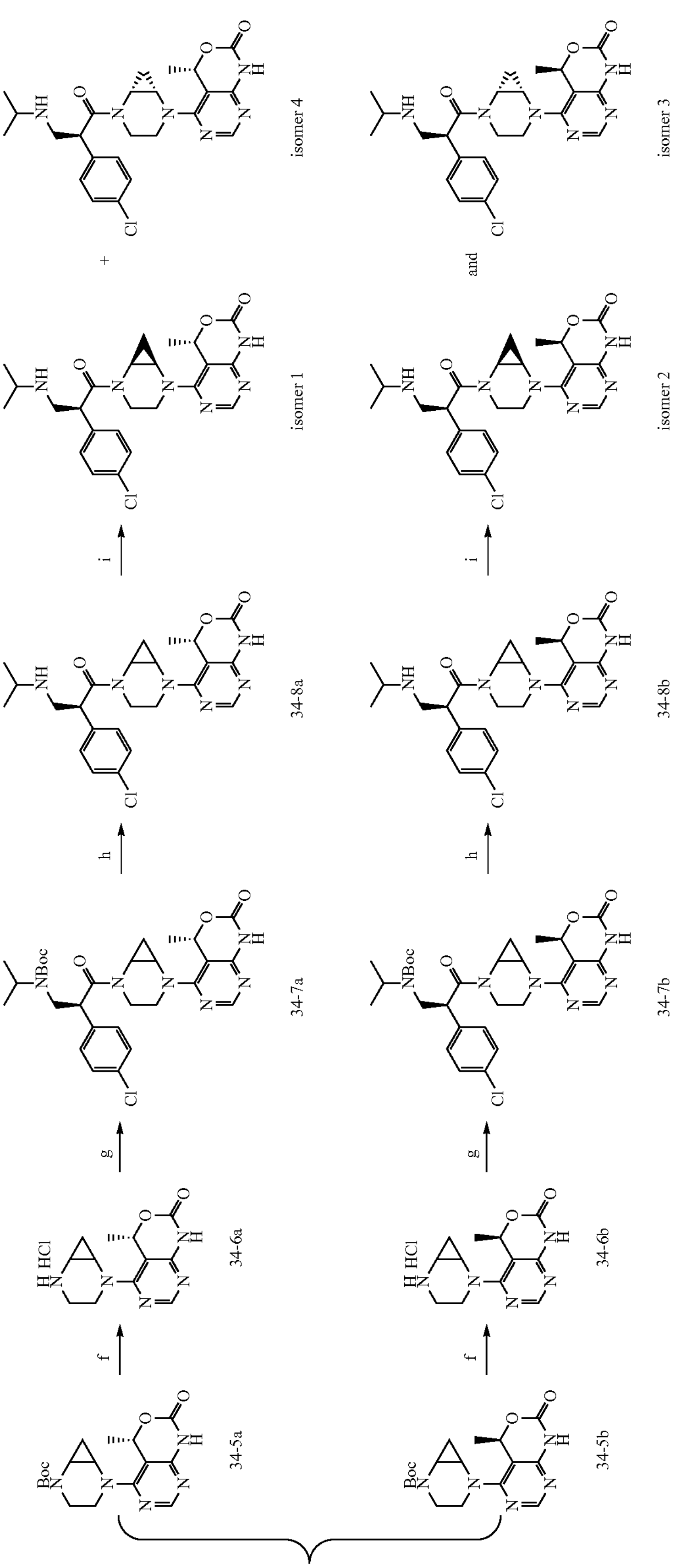
34-5a 34-6a 34-7a 34-8a isomer 1 + isomer 4
34-5b 34-6b 34-7b 34-8b isomer 2 and isomer 3 a) 1-(4-amino-6-chloropyrimidin-5-yl) ethanone (compound 34-1)

1-(4,6-dichloropyrimidin-5-yl) ethanone (2.5 g) was dissolved in tetrahydrofuran (15 mL) at 20° C., ammonia water (25-28 wt %, 9 g) was added, the reaction solution was stirred at 20° C. for 5 h, concentrated, diluted with a small amount of water, subjected to suction filtration, and dried in vacuum to yield a white solid (2 g) that was directly used at the next step.

b) 1-(4-amino-6-chloropyrimidin-5-yl) ethan-1-ol (compound 34-2)

1-(4-amino-6-chloropyrimidin-5-yl) ethanone (1.5 g) was dissolved in methanol (15 mL) at 20° C., the solution was cooled to −10° C., sodium borohydride (1 g) was added in batches, and the reaction solution was slowly heated to 20° C. and stirred for 3 h. After the reaction was completed, the reaction was quenched with a saturated ammonium chloride aqueous solution. Then, the reaction solution was concentrated and beaten with ethyl acetate (20 mL×2). The mother solution was concentrated to yield an oily crude product. The crude product was separated by column chromatography to yield a white oily product (400 mg). LC-MS (ESI) m/z: 174 (M+H). c) 5-chloro-4-methyl-1,4-dihydro-2H-pyrimidin[4,5-d][1,3]oxazin-2-one (compound 34-3) 1-(4-amino-6-chloropyrimidin-5-yl) ethan-1-ol (300 mg) and N,N-diisopropylethylamine (282 mg) were dissolved in tetrahydrofuran (3 mL) at 20° C., the solution was cooled to −5° C., bis(trichloromethyl) carbonate (300 mg) was slowly added, and the reaction solution was stirred at −5° C. for 0.5 h. Then, the reaction solution was slowly heated to 18° C. and stirred for 1.5 h. After the reaction was completed, the reaction was quenched with a sodium bicarbonate aqueous solution, the reaction solution was extracted with ethyl acetate (10 mL×3), organic phases were combined, and a combined organic phase was dried with anhydrous sodium sulfate, filtered, and concentrated to yield an oily crude product. The crude product was separated and purified by column chromatography to yield a white solid (108 mg). LC/MS (ESI) m/z: 200 (M+H).

d)(S)-5-chloro-4-methyl-1,4-dihydro-2H-pyrimidin[4,5-d][1,3]oxazin-2-one (compound 34-4a) and (R)-5-chloro-4-methyl-1,4-dihydro-2H-pyrimidin[4,5-d][1,3]oxazin-2-one (compound 34-4b) Compound 34-3 was subjected to SFC chiral resolution to yield required target compound 34-4a and compound 34-4b.

SFC chiral resolution conditions were as follows: instrument: waters SFC200; separation column: Daicel Chiralcel AD, 250×50 mm I.D., 10 um; mobile phases: A: $CO_2$, B: methanol (0.1 vol % of ammonia water (25-28 wt %)), and A: B-65:35 (volume ratio); flow rate: 150 mL/min; pressure: 100 bar; column temperature: 38° C.; detection wavelength: 220 nm; cycle time: 14 min; sample pre-treatment: 10 g of sample was dissolved in 300 mL of MeOH; and injection volume: 16 mL. Post-treatment: the sample was concentrated at 40° C. and lyophilized to yield compound 34-4a and compound 34-4b, respectively.

Route 1: preparation of isomer 1 and isomer 4 e) Tert-butyl 5-((S) 4-methyl-2-oxo-1,4-dihydro-2H-pyrimidinyl[4,5-d][1,3]oxazin-5-yl)-2,5-diazabicyclo[4.1.0]heptane-2-carboxylate (compound 34-5a)

Compound 34-4a (2 g) and tert-butyl 2,5-diazabicyclo[4.1.0]heptane-2-carboxylate (3.58 g) were dissolved in anhydrous MeCN (20 mL), DIEA (3.89 g) was added, the reaction solution was purged with nitrogen gas, sealed, and stirred at 95° C. for 6 h, and after the reaction was completed, the reaction solution was concentrated to yield a target crude product. The crude product was dissolved in DCM, washed with water, and concentrated to yield a crude product, and the crude product was separated and purified by column chromatography (EA:PE=1:1) to yield a light brown solid (3.2 g).

f)(4S)-5-(2,5-diazabicyclo[4.1.0]heptan-2-yl)-4-methyl-1,4-dihydro-2H-pyrimido[4,5-d][1,3]oxazin-2-one hydrochloride (compound 34-6a)

The product (3.2 g) obtained at step e) was dissolved in HCl/i-PrOH (10 mL), the reaction solution was stirred at the room temperature for 2 h, and after the reaction was completed, the reaction solution was concentrated to yield a crude product that was not purified and directly used at the next step.

g) Compound 34-7a

The product (3.3 g) obtained at step f), (S)-3-((tert-butoxycarbonyl)(isopropyl)amino)-2-(4-chlorophenyl) propanoic acid (4.9 g), HATU (6.32 g), and DIPEA (4.3 g) were dissolved in anhydrous DMF (50 mL), the reaction solution was stirred at the room temperature for 12 h, after the reaction was completed, the reaction solution was poured into ethyl acetate (100 mL), and washed with water (20 mL×3) and a saturated salt solution (10 mL), and an obtained organic phase was dried and concentrated to yield a crude product. The crud product was separated and purified by column chromatography (PE:EA=1:1) to yield a brown solid (7.2 g). MS (ESI) m/z: 585 (M+H).

h) Compound 34-8a

The product (7.2 g) obtained at step g) was dissolved in MeOH (25 mL), HCl/dioxane (70 mL) was added, the reaction solution was stirred at the room temperature for 2 h and concentrated to yield a red oily crude product, and the crude product was dissolved in MeOH (20 mL), freed with $Na_2CO_3$, and concentrated to yield a crude product (6 g).

i) Isomer 1 and isomer 4

Compound 34-8a was subjected to SFC chiral resolution to yield isomer 1 and isomer 4. SFC resolution conditions: instrument: waters SFC200; separation column: Daicel Chiralcel AD, 250×50 mm I.D., 10 um; mobile phases: A: $CO_2$, B: MeOH (0.1 vol % of ammonia water (25-28 wt %)), and A: B=75:25; flow rate: 70 mL/min; pressure: 100 bar; column temperature: 38° C.; detection wavelength: 254 nm; cycle time: 5 min; sample pre-treatment: 10 g of sample was dissolved in 200 mL of MeOH; and injection volume: 16 mL.

Post-treatment: the sample was concentrated at 40° C. and lyophilized to yield isomer 1 and isomer 4, respectively.

Route 2: Preparation of Isomer 2 and Isomer 3

Isomer 2 and isomer 3 were respectively prepared from compound 34-4b serving as a raw material by the method described in route 1.

Isomer 1: LC-MS m/z: 485 (M+H). $^1$H NMR (400 MHz, DMSO-$d_6$) δ 10.70 (s, 1H), 8.23 (s, 1H), 7.46 (d, J=8.5 Hz, 2H), 7.39 (d, J=8.6 Hz, 2H), 6.13 (q, J-6.6 Hz, 1H), 4.51 (s, 1H), 4.42-4.30 (m, 1H), 3.53-3.45 (m, 1H), 3.28-3.06 (m, 5H), 3.01-2.59 (m, 3H), 1.52-1.34 (m, 4H), 1.08-0.97 (m, 6H), 0.93-0.84 (m, 1H).

Isomer 4: LC-MS m/z: 485 (M+H). $^1$H NMR (400 MHz, DMSO-$d_6$) δ 10.73 (s, 1H), 8.23 (s, 1H), 7.41-7.32 (m, 4H), 6.14 (q, J=8.0 Hz, 1H), 4.40-4.36 (m, 1H), 4.19-4.11 (m, 1H), 3.62-3.51 (m, 2H), 3.49-3.35 (m, 1H), 3.24-3.05 (m, 4H), 2.73-2.63 (m, 2H), 1.45 (d, J=8.0 Hz, 1H), 1.33 (d, J=8.0 Hz, 2H), 1.12 (q, J=4.0 Hz, 1H), 0.95-0.88 (m, 6H), 0.26 (q, J=4.0 Hz, 1H).

Isomer 2: LC-MS m/z: 485 (M+H). H NMR (400 MHz, DMSO-$d_6$) δ 10.86 (s, 1H), 8.27 (s, 1H), 7.54-7.27 (m, 4H), 6.32-6.18 (m, 1H), 4.69-4.52 (m, 1H), 4.27-3.97 (m, 2H), 3.66-3.43 (m, 2H), 3.29-2.92 (m, 6H), 2.61-2.55 (m, 1H), 1.63-1.58 (m, 1H), 1.53-1.28 (m, 3H), 1.28-1.12 (m, 6H).

Isomer 3: LC-MS m/z: 485 (M+H). $^1$H NMR (400 MHz, DMSO-$d_6$) δ 10.71 (s, 1H), 8.18 (s, 1H), 7.46-7.39 (m, 1H), 7.36-7.28 (m, 3H), 6.00 (q, J=6.4 Hz, 1H), 4.53 (s, 1H), 4.46-4.33 (m, 1H), 3.56-3.44 (m, 2H), 3.26-3.09 (m, 5H), 3.00-2.71 (m, 2H), 1.43-1.38 (m, 3H), 1.10-0.93 (m, 7H), −0.07--0.11 (m, 1H).

Determination of Configurations by Single Crystal Diffraction:

(1) Determination of a Configuration of Isomer 1

Preparation of a single crystal: compound isomer 1 (50.0 mg) and isopropanol (3.0 mL) were weighed and placed in a 5 mL screw flask and stirred for 5 min until the solid was fully dissolved. Oxalic acid dihydrate (13.0 mg) was weighed and placed in the above flask, a white solid was gradually precipitated in the flask, the reaction solution was stirred at the room temperature for 3 h, and a large amount of white solid was precipitated in the flask. Methanol (1.5 mL) and purified water (0.2 mL) were placed in the flask, the white solid gradually disappeared, and after becoming clear, the solution was stirred for 1 h. The solution was filtered with a 0.22 μm microfiltration membrane to a 20 mL screw flask, and the opening of the flask was covered with a plastic wrap. The plastic warp covering the opening of the flask was pierced by using a needle to form 8 small holes, the flask was placed at the room temperature for 10 d, and an oxalate single crystal of isomer 1 was obtained.

Single crystal diffraction experiment:

Single crystal X-ray diffractometer: BRUKER KAPPA APEX-II CCD Wavelength: Cu Kα (λ=1.54178 Å)

Test temperature: 296 K

Computer program for structural analysis: SHELXL-2018

Single crystal data: molecular formula: $C_{50}H_{60}Cl_2N_{12}O_{10}$; molecular weight: 1060.00; crystal system: orthorhombic crystal system; space group: C222; cell parameters: a=15.719 (2) Å, b-17.411 (2) Å, c-48.335 (6) Å, α=90°, β-90°, and γ-90°; unit cell volume: V=13228 (3) Å3; the number of molecular formulas contained in the unit cell: Z-8; calculated density: $D_{calc}$=1.064 g/cm$^3$; R (F.): 0.0612; $R_W(F_o^2)$: 0.1856; goodness of fit(S): 1.023; and Flack parameter: 0.040 (11).

Figure 3:
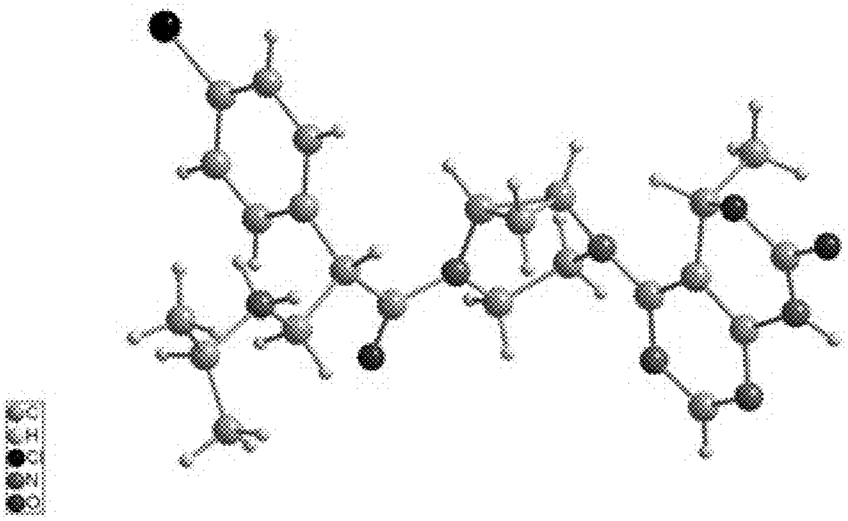
FIG. 3 is a schematic diagram of a single molecule of isomer 1 of Example 3.
Figure 4:
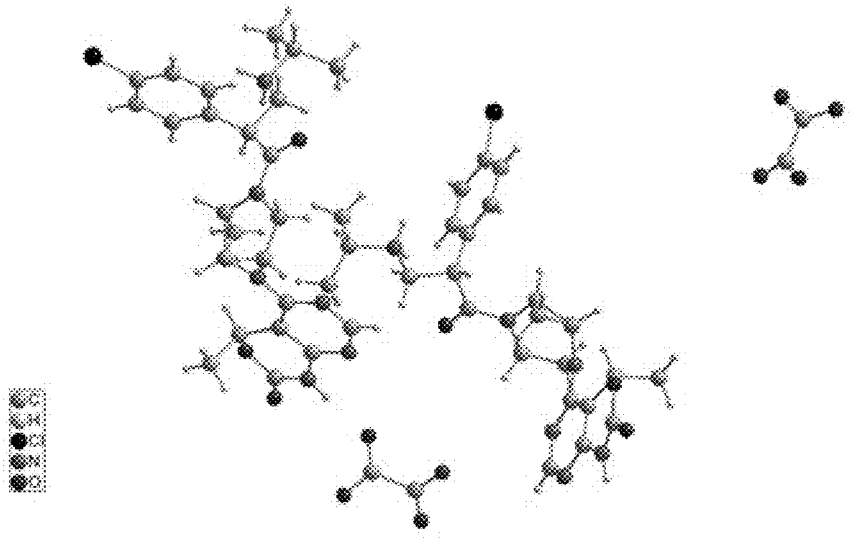
FIG. 4 is a schematic diagram of asymmetric structural unit of an oxalate single crystal of isomer 1 of Example 3.

Structural description: single crystal X-ray diffraction and structural analysis show that the prepared single crystal is an oxalate of isomer 1. Asymmetric structural unit of the crystal include two isomer molecules and one oxalic acid molecule. The single molecule of compound isomer 1 is shown in FIG. 3, and the oxalate single crystal is shown in FIG. 4. The structural formula is shown below:

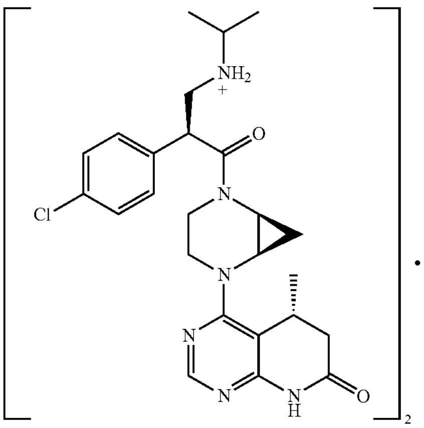

(2) Determination of a Configuration of Isomer 3

Preparation of a single crystal: an oxalate single crystal of isomer 3 was prepared by the above preparation method of the single crystal of isomer 1.

Single crystal diffraction experiment:

Single crystal X-ray diffractometer: BRUKER D8 VENTURE PHOTON II

Wavelength: Ga Kα (2=1.34139 Å)

Test temperature: 173 K

Computer program for structural analysis: SHELXL-2018

Single crystal data: molecular formula: $C_{52}H_{64}Cl_2N_{12}O_{15}$; molecular weight: 1168.05; crystal system: monoclinic crystal system; space group: P21/c; cell parameters: a=20.1588 (13) Å, b=21.4744 (14) Å, c=14.4055 (9) Å, α=90°, β=98.259 (3)°, and γ=90°; unit cell volume: V=6171.4 (7) Å3; the number of molecular formulas contained in the unit cell: Z-4; calculated density: $D_{calc}$=1.257 g/cm$^3$; R($F_o$): 0.0634; $R_W(F_o^2)$: 0.2016; and goodness of fit(S): 1.053.

Figure 5:
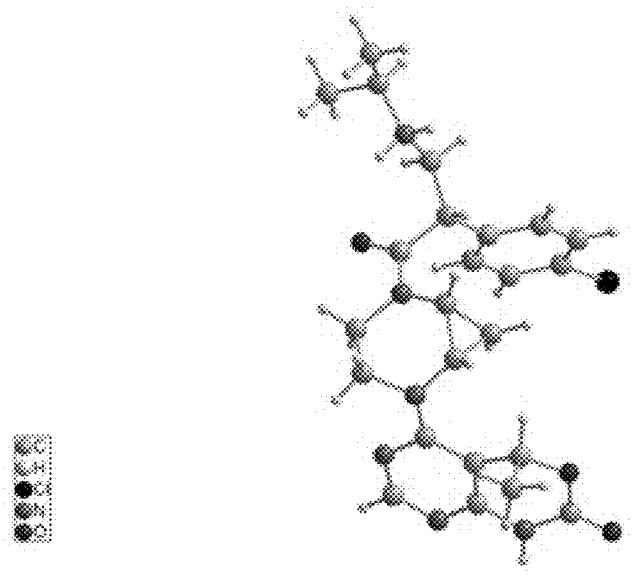
FIG. 5 is a schematic diagram of a single molecule of isomer 3 of Example 3.
Figure 6:
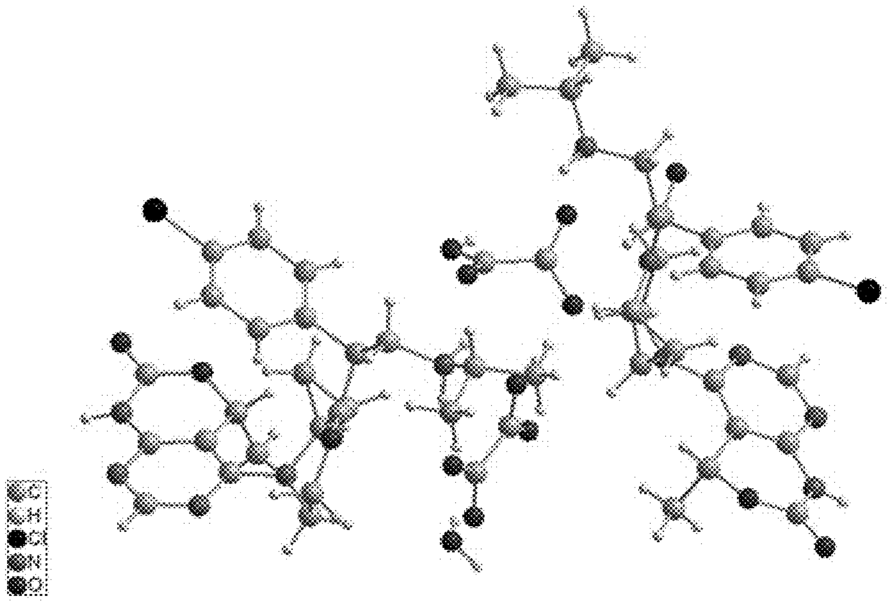
FIG. 6 is a schematic diagram of asymmetric structural unit of an oxalate single crystal of isomer 3 of Example 3.

Structural description: single crystal X-ray diffraction and structural analysis show that the prepared single crystal is an oxalate hydrate of isomer 3. Asymmetric structural unit of the crystal include two isomer 3 molecules, two oxalic acid molecules, and one water molecule, wherein isomer 3 and oxalic acid form an oxalate. The single molecule of compound isomer 3 is shown in FIG. 5, and the asymmetric structural unit of the oxalate single crystal is shown in FIG. 6. The structural formula is shown below:

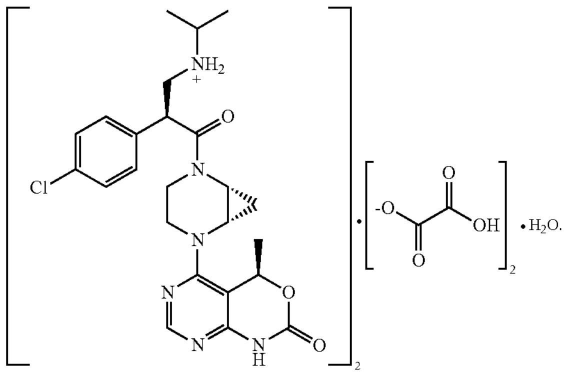

Pharmacological Activity Assay

Example 4 AKT Kinase Activity Assay

1. Materials and Reagents

Envision model plate reader (Molecular Devices)

White 384-well plate (Thermo, Art. No. #264706)

Main reagents included in an HTRF kinEASE TK kit (Cisbio, Art. No. #62TKOPEC)

TK-biotin substrate

Streptavidin-XL665

Europium-labeled tyrosine kinase substrate antibody

5× enzyme reaction buffer

SEB

HTRF assay buffer

AKT1 (Carna, Art. No. #01-101)

AKT2 (Carna, Art. No. #01-102)

AKT3 (Invitrogen, Art. No. #PV3185)

10 mM ATP (Invitrogen, Art. No. #PV3227)

1 MDTT (Sigma, Art. No. #D5545)

1 M $MgCl_2$ (Sigma, Art. No. #M8266)

The compounds of Examples 1 to 3 of the present application

Positive control: GDC-0068

2. Experimental Procedure 2.1 Preparation of Reagents

TABLE 1

| Concentrations of components of kinase reaction systems | | | | |
|---|---|---|---|---|
| Reaction reagent | | AKT1 | AKT2 | AKT3 |
| Concentration of enzyme | Final concentration at the enzyme reaction step (10 μL) | 0.6 ng/well | 0.1 ng/well | 0.3 ng/well |
| Concentration of ATP | | 2 μM | 20 μM | 10 nM |
| Concentration of TK-biotin substrate | | 2 μM | 2 μM | 2 μM |
| Enzyme reaction time | | 50 min | 50 min | 50 min |
| Concentration of streptavidin-XL665 | Final concentration in the overall reaction (20 μL) | 125 nM | 125 nM | 125 nM |
| Concentration of europium-labeled tyrosine kinase substrate antibody | | 1:100 diluted | 1:100 diluted | 1:100 diluted |

1×kinase reaction buffer

A 1× kinase reaction buffer for 1 mL of kinase AKT1, AKT2 or AKT3 included 200 μL of 5× kinase reaction buffer, 5 μL of 1 M $MgCl_2$, 1 μL of 1 M DTT, and 794 μL of ultra-pure water.

5× TK-biotin substrate and ATP working solution

Specific concentrations of the TK-biotin substrate and ATP are shown in Table 1.

The substrate and ATP were respectively diluted with the 1× kinase reaction buffer to a concentration 5 times the reaction concentration.

5× kinase working solution

The concentration for enzyme screening is shown in Table 1. A 5× enzyme working solution was prepared from the 1×kinase reaction buffer.

4×streptavidin-XL665 working solution

The concentration of streptavidin-XL665 in the reaction is shown in Table 1. A 4× streptavidin-XL665 working solution was prepared from the assay buffer.

4×europium-labeled tyrosine kinase substrate antibody working solution

The europium-labeled tyrosine kinase substrate antibody was 100-fold diluted with the assay reaction buffer to obtain a working solution.

2.2 Experimental Process

After all the reagents were prepared according to the above method, except for the enzyme, the reagents were equilibrated to the room temperature and loaded.

a) first, a compound stock solution (10 mM DMSO solution) was diluted with DMSO to obtain a 100 μM compound solution, the compound solution was diluted with the 1× kinase reaction buffer to obtain a 2.5 μM compound working solution (containing 2.5% DMSO). A 2.5% DMSO solution was prepared from the 1×kinase reaction buffer, and the 2.5 μM compound working solution was diluted 7 times with the 2.5% DMSO solution according to a 4-fold gradient to obtain compound working solutions at 8 concentrations (2500 nM, 625 nM, 156 nM, 39 nM, 9.8 nM, 2.4 nM, 0.6 nM, and 0.15 nM). Except for control wells, 4 μL of diluted compound working solution was placed in each reaction well, and 4 μL of previously prepared 2.5% DMSO/kinase buffer was placed in each control well.

b) 2 μL of previously prepared TK-biotin substrate solution (the concentration of the substrate for enzyme screening is shown in Table 1) was placed in each reaction well.

c) 2 μL of previously prepared enzyme solution (the concentration of the enzyme is shown in Table 1) was placed in each reaction well except for negative wells, and 2 μL of 1×kinase reaction buffer corresponding to the enzyme was placed in each negative well to make up the volume. The plate was sealed with a sealing film, and the reaction solution was mixed until uniform and incubated at the room temperature for 10 min to allow the compound to fully react with and bind to the enzyme.

d) 2 μL of ATP solution was placed in each reaction well to initiate a kinase reaction (the concentration of ATP for enzyme screening and reaction time are shown in Table 1).

e) 5 min before the kinase reaction was completed, an assay solution was prepared. Streptavidin-XL665 and a europium-labeled tyrosine kinase substrate antibody (1:100) assay solution (the concentration of the assay reagent is shown in Table 1) were prepared from the assay buffer in the kit.

f) After the kinase reaction was completed, 5 μL of diluted streptavidin-XL665 was placed in each reaction well and mixed with the reaction solution until uniform, and the diluted europium-labeled tyrosine kinase substrate antibody assay solution was immediately added.

g) The plate was sealed, the reaction solution was mixed until uniform and reacted at the room temperature for 1 h, and fluorescence signals were detected by using an ENVISION (Perkinelmer) instrument (320 nm stimulation, 665 nm, 615 nm emission). An inhibition rate in each well was calculated from all active wells and background signal wells, a mean value of repetitive wells was calculated, and the half inhibitory activity (IC50) of each compound to be tested was fitted by using the professional drawing analysis software PRISM 6.0.

TABLE 2

| Experimental loading process | | | |
|---|---|---|---|
| | Kinase reaction system | Control group | |
| Enzyme reaction step (10 μL) | Sample group | Negative control | Positive control |
| Compounds of Examples 1 to 3 | 4 μL | 4 μL of 2.5% DMSO/kinase buffer | 4 μL of 2.5% DMSO/kinase buffer |
| TK-biotin-labeled substrate | 2 μL | 2 μL | 2 μL |
| Kinase | 2 μL | 2 μL of kinase buffer | 2 μL |
| Seal with a film, and incubate at the room temperature for 10 min | | | |
| ATP | 2 μL | 2 μL | 2 μL |
| Seal with a film, and incubate at the room temperature for 50 min | | | |
| Detection steps (10 μL) | | | |
| Streptavidin-XL665 | 5 μL | 5 μL | 5 μL |
| Europium-labeled tyrosine kinase substrate antibody | 5 μL | 5 μL | 5 μL |
| Seal with a film, and incubate at the room temperature for 1 h | | | |
| Detection light: 320 nm, emitted light: 665 nm, 615 nm | | | |

2.3 Data Analysis

ER=fluorescence value at 665 nm/fluorescence value at 615 nm

Inhibition rate=$(ER_{positive\ control}-ER_{sample})/(ER_{positive\ control}-ER_{negative\ control})\cdot 100\%$ 3. Experimental Results Experimental results are shown in Table 3.

TABLE 3

| AKT inhibiting activity | | | | |
|---|---|---|---|---|
| Compound | Chemical structure | AKT1 enzyme activity $IC_{50}$ (nM) | AKT2 enzyme activity $IC_{50}$ (nM) | AKT3 enzyme activity $IC_{50}$ (nM) |
| Isomer 1 of Example 1 | 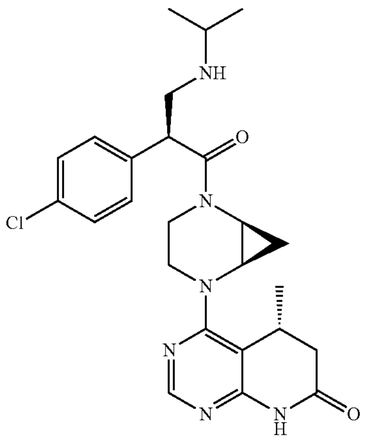 Isomer 1 | 62 | 542 | 13 |

TABLE 3-continued
| AKT inhibiting activity | | | | |
|---|---|---|---|---|
| Compound | Chemical structure | AKT1 enzyme activity $IC_{50}$ (nM) | AKT2 enzyme activity $IC_{50}$ (nM) | AKT3 enzyme activity $IC_{50}$ (nM) |
| Isomer 2 of Example 1 | 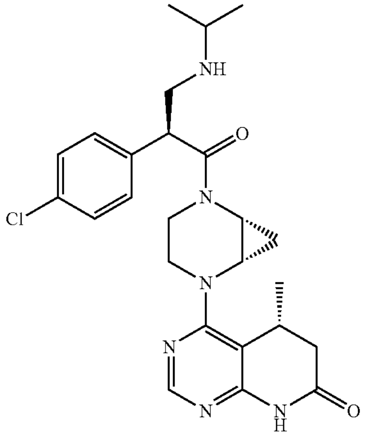 Isomer 2 | 0.35 | 6.3 | 0.09 |
| Isomer 1 of Example 2 | 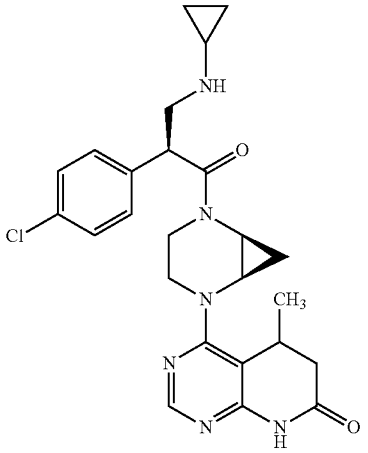 Isomer 1 | 442 | 1000 | 59 |
| Isomer 2 of Example 2 | 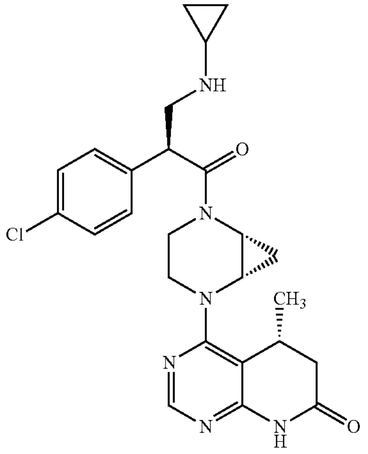 Isomer 2 | 0.65 | 5.7 | 0.12 |

TABLE 3-continued
| AKT inhibiting activity | | | | |
|---|---|---|---|---|
| Compound | Chemical structure | AKT1 enzyme activity $IC_{50}$ (nM) | AKT2 enzyme activity $IC_{50}$ (nM) | AKT3 enzyme activity $IC_{50}$ (nM) |
| Isomer 1 of Example 3 | 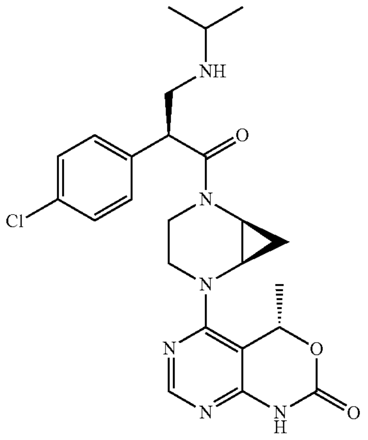 Isomer 1 | 186 | 771 | 45 |
| Isomer 2 of Example 3 | 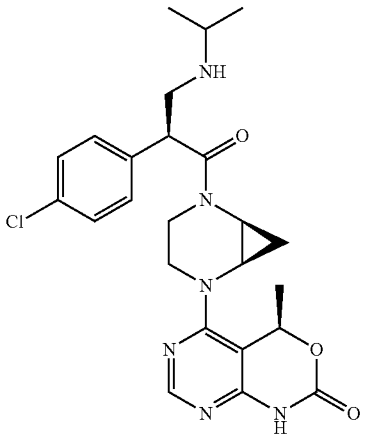 Isomer 2 | 613 | 1000 | 89 |
| Isomer 3 of Example 3 | 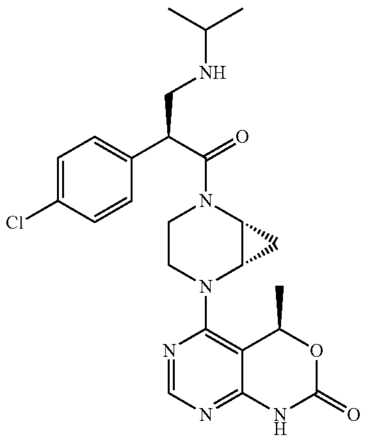 Isomer 3 | 429 | 1000 | 232 |

TABLE 3-continued

| AKT inhibiting activity | | | | |
|---|---|---|---|---|
| Compound | Chemical structure | AKT1 enzyme activity $IC_{50}$ (nM) | AKT2 enzyme activity $IC_{50}$ (nM) | AKT3 enzyme activity $IC_{50}$ (nM) |
| Isomer 4 of Example 3 | 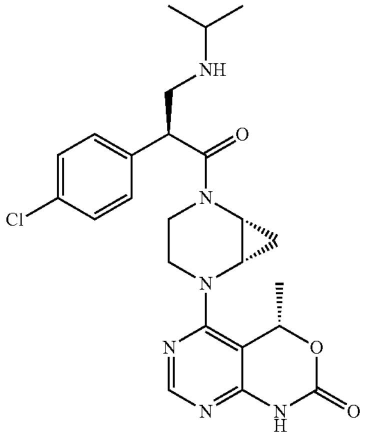 Isomer 4 | 0.6 | 1.2 | 0.12 |
| Positive control GDC-0068 | 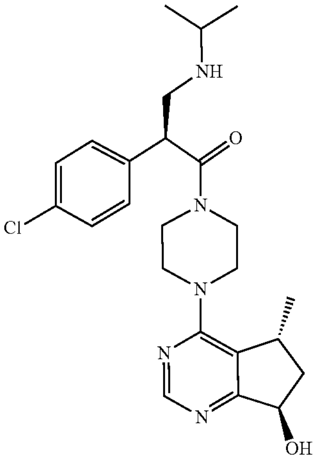 [SMILES: CC(C)NC[C@@H](C(=O)N1CCN(c2ncnc3c2[C@H](C)C[C@H]3O)CC1)c1ccc(Cl)cc1] | 3.2 | 1.7 | 2.5 |

Example 5 Pharmacodynamics Evaluation of the Compound of the Present Application in a Subcutaneous Transplantation Model of LnCap Human Prostate Cancer 1. Experimental Materials 1.1 Experimental Animals NCG mice, male, 8-10-week-old (when tumor cells were inoculated into the mice). The mice were purchased from Jiangsu GemPharmatech Co., Ltd. Breeding environment: SPF level.

1.2 Test Samples and Control

Test samples: isomer 2 of Example 1 (hereinafter referred to as compound 62)

isomer 2 of Example 2 (hereinafter referred to as compound 98)

isomer 4 of Example 3 (hereinafter referred to as compound 102)

Positive control: GDC-0068

1.3 Reagents

Androgen pills, manufacturer: aladdin, Art. No.: A1910098.

FBS, manufacturer: Gibco, Art. No.: 10099141C.

RPMI1640 medium, manufacturer: Gibco, Art. No.: C22400500BT.

Matrigel, manufacturer: Corning, Art. No.: 354234.

PBS, manufacturer: Crownbio, Art. No.: 20190828.

2. Experimental Method and Procedure 2.1 Cells

LnCap cells were cultured in an RPMI1640 medium containing 10 vol % of fetal bovine serum (FBS). LnCap cells in exponential growth phase were harvested and resuspended in PBS to a concentration suitable for subcutaneous tumor inoculation into mice.

2.2 Construction of Animal Models and Grouping

One day before inoculation of cells, androgen pills were subcutaneously implanted into all animals, and the whole process was sterile. $1\times10^7$ LnCap cells were subcutaneously inoculated into each experimental mouse, the cells were resuspended in a mixture of PBS and matrigel in a ratio of 1:1 (0.2 mL/mouse), the tumor growth was monitored regularly, and after tumors grew to an average volume of 177.70 $mm^3$, the mice were randomly grouped according to the tumor size and mouse weight and administered (see Table 4). A formula for calculating a tumor volume: long diameter×short diameter$^2$/2.

TABLE 4

LnCap animal model groups

| Group | Number of experimental animals n (head) | Administration | Dose (mg/kg) |
|---|---|---|---|
| 1 | 10 | Solvent control | — |
| 2 | 10 | Compound 62 | 12.5 |
| 3 | 10 | Compound 62 | 25 |
| 4 | 10 | Compound 62 | 50 |
| 5 | 10 | GDC-0068 | 25 |
| 6 | 6 | Compound 98 | 50 |
| 7 | 6 | Compound 102 | 50 |

2.3 Preparation of Medicaments

The compounds of the present application and the positive control were dissolved in solvents to obtain solutions of compound 62 at concentrations of 1.25 mg/mL, 2.5 mg/mL, and 5 mg/mL, a solution of the positive control at a concentration of 2.5 mg/mL, a solution of compound 98 at a concentration of 5 mg/mL, and a solution of compound 102 at a concentration of 5 mg/mL, respectively.

Solvent: the solvent was a mixed solvent of PG, PEG400, and water, PG: PEG400: water-(20-40):(20-30):(30-50)(v: v: v). Any ratio within the range can be used.

2.4 Dosage Regimen

Specific dosage regimens are shown in Table 5.

TABLE 5

Administration routes, doses, and regimens for LnCap animal models

| Group | Number of experimental animals n (head) | Administration | Dose (mg/kg) | Administration frequency | Administration method | Administration days |
|---|---|---|---|---|---|---|
| 1 | 10 | Solvent control | — | QD | po | 18 days |
| 2 | 10 | Compound 62 | 12.5 | QD | po | 18 days |
| 3 | 10 | Compound 62 | 25 | QD | po | 18 days |
| 4 | 10 | Compound 62 | 50 | QD | po | 18 days |
| 5 | 10 | GDC-0068 | 25 | QD | po | 18 days |
| 6 | 6 | Compound 98 | 50 | QD | po | 18 days |
| 7 | 6 | Compound 102 | 50 | QD | po | 18 days |

2.5 Data Analysis

All experimental results are shown as mean tumor volume±SEM (standard error of mean). Whether there is a significant difference between the treatment group and the control group in terms of tumor volume was determined by the independent samples T test. All data were analyzed by using SPSS 18.0. P<0.05 indicates a significant difference.

T/C (%)=mean tumor volume of a treatment group/mean tumor volume of a control group x 100%; and

TGI (%)=(1-T/C)×100%.

2.6 Experimental Results

The growth of tumors in the treatment groups and the control group is shown in Table 6.

TABLE 6

Efficacy analysis in models of LnCap human prostate cancer in treatment groups

| | Experimental group | TV on the day of grouping and administration ($mm^3$) | TV on the day of the end of the experiment ($mm^3$) | TGI (%) | T/C (%) | P value* |
|---|---|---|---|---|---|---|
| 1 | Solvent control | 177.78 ± 6.66 | 964.70 ± 133.75 | — | — | — |
| 2 | Compound 62 (12.5 mg/kg) | 177.76 ± 6.67 | 401.07 ± 80.17 | 58.43 | 41.57 | 0.007 |

TABLE 6-continued

| Efficacy analysis in models of LnCap human prostate cancer in treatment groups | | | | | | |
|---|---|---|---|---|---|---|
| | Experimental group | TV on the day of grouping and administration ($mm^3$) | TV on the day of the end of the experiment ($mm^3$) | TGI (%) | T/C (%) | P value* |
| 3 | Compound 62 (25 mg/kg) | 177.80 ± 6.71 | 153.42 ± 23.11 | 84.10 | 15.90 | <0.001 |
| 4 | Compound 62 (50 mg/kg) | 177.78 ± 6.64 | 43.64 ± 16.62 | 95.48 | 4.52 | <0.001 |
| 5 | GDC-0068 (25 mg/kg) | 177.76 ± 6.52 | 488.03 ± 81.68 | 49.41 | 50.59 | 0.006 |
| 6 | Compound 98 (50 mg/kg) | 177.61 ± 8.92 | 187.49 ± 22.88 | 80.56 | 19.44 | <0.001 |
| 7 | Compound 102 (50 mg/kg) | 177.90 ± 10.06 | 99.30 ± 40.55 | 89.71 | 10.29 | <0.001 |

*treatment group vs. solvent control group

The inventors have found that compound I-0 of the present application has an inhibiting effect on the AKT kinase activity, especially compound I of the present application (i.e., isomer 2 of Example 1, isomer 2 of Example 2, and isomer 4 of Example 3), which shows an obvious tumor inhibiting effect in the in vivo experiment. Therefore, the compounds and the pharmaceutical compositions comprising the compounds of the present application can be used for preventing and/or treating an AKT protein kinase-mediated disease or disease state. Further, the inventors have found that if a dosage of the pharmaceutical composition administered to the subject in need that is calculated based on compound I-0 or compound I is 0.001-100 mg/kg weight/day, preferably 0.01-50 mg/kg weight/day, and more preferably 10-50 mg/kg weight/day, the pharmaceutical composition can obviously inhibit the tumor growth.

Example of Preparation

Exemplary preparations of the present application are provided below. It is to be understood that the following preparations can be prepared by the conventional preparation method in the art that is well known to those skilled in the art.

Preparation 1: capsule containing 25 mg of compound 62

| Component | Mass ratio | Usage amount for a unit dosage (mg) |
|---|---|---|
| Compound 62 | 25.00% | 25.00 |
| Anhydrous calcium hydrogen phosphate | 74.00% | 74.00 |
| Glyceryl behenate | 1.00% | 1.00 |
| Total weight | 100.00% | 100.00 |

a) Compound 62, anhydrous calcium hydrogen phosphate, and glyceryl behenate are added to a mixer hopper and mixed until uniform; and b) the mixture is filled into a capsule.

Preparation 2: capsule containing 50 mg of compound 62

| Component | Mass ratio | Usage amount for a unit dosage (mg) |
|---|---|---|
| Compound 62 | 33.33% | 50.00 |
| Anhydrous calcium hydrogen phosphate | 65.67% | 98.50 |
| Glyceryl behenate | 1.00% | 1.50 |
| Total weight | 100.00% | 150.00 |

Preparation 2 is prepared by the preparation method of preparation 1.

Preparation 3: capsule containing 100 mg of compound 62

| Component | Mass ratio | Usage amount for a unit dosage (mg) |
|---|---|---|
| Compound 62 | 41.67% | 100.00 |
| Calcium hydrogen phosphate dihydrate | 57.33% | 137.60 |
| Glyceryl behenate | 1.00% | 2.40 |
| Total weight | 100.00% | 240.00 |

Preparation 3 is prepared by the preparation method of preparation 1.

Preparation 4: capsule containing 150 mg of compound 62

| Component | Mass ratio | Usage amount for a unit dosage (mg) |
|---|---|---|
| Compound 62 | 62.50% | 150.00 |
| Calcium hydrogen phosphate dihydrate | 36.50% | 87.60 |
| Glyceryl behenate | 1.00% | 2.40 |
| Total weight | 100.00% | 240.00 |

Preparation 4 is prepared by the preparation method of preparation 1.

Preparation 5: capsule containing 200 mg of compound 62

| Component | Mass ratio | Usage amount for a unit dosage (mg) |
|---|---|---|
| Compound 62 | 62.50% | 200.00 |
| Calcium hydrogen phosphate dihydrate | 36.50% | 116.8 |
| Glyceryl behenate | 1.00% | 3.2 |
| Total weight | 100.00% | 320.00 |

Preparation 5 is prepared by the preparation method of preparation 1.

Preparation 6: dry suspension containing 400 mg of compound 62

| Component | Mass ratio | Usage amount for a unit dosage (mg) |
|---|---|---|
| Compound 62 | 62.50% | 400.00 |
| Calcium hydrogen phosphate dihydrate | 36.50% | 233.6 |
| Glyceryl behenate | 1.00% | 6.4 |
| Total weight | 100.00% | 640.00 |

a) Compound 62, calcium hydrogen phosphate dihydrate, and glyceryl behenate are added to a mixer hopper and mixed until uniform; and b) the mixture is filled into an aluminum bag to form a dry suspension.

The above are preferred embodiments of the present application only, but are not intended to limit the present application. Any modification, equivalent replacement, and improvement made within the spirit and principle of the present application shall fall within the protection scope of the present application.

What is claimed is:

1. A unit dosage pharmaceutical composition comprising compound I-0 or a pharmaceutically acceptable salt thereof, wherein the mass of the compound I-0 or the pharmaceutically acceptable salt thereof is 5 mg to 400 mg calculated as a free base, and the compound I-0 has the following structure:

I-0

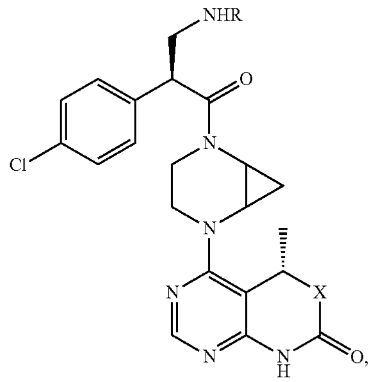

wherein, R is selected from the group consisting of C1-C4 alkyl and C3-C6 cycloalkyl; and X is selected from the group consisting of $CH_2$ and O.

2. The unit dosage pharmaceutical composition according to claim 1, wherein the compound I-0 is selected from the group consisting of:

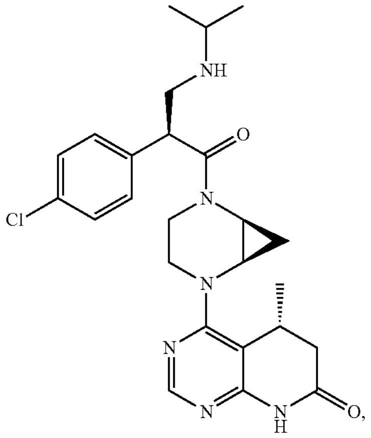

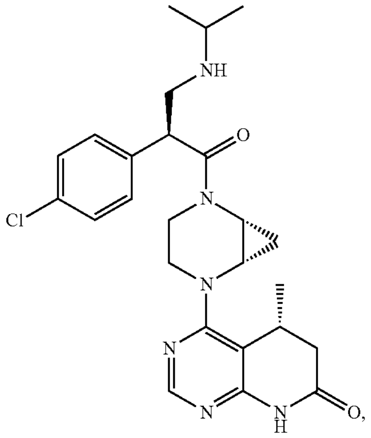

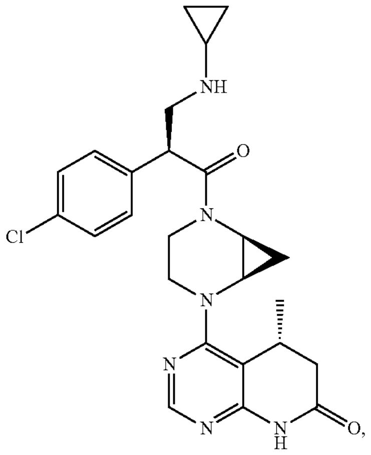

-continued

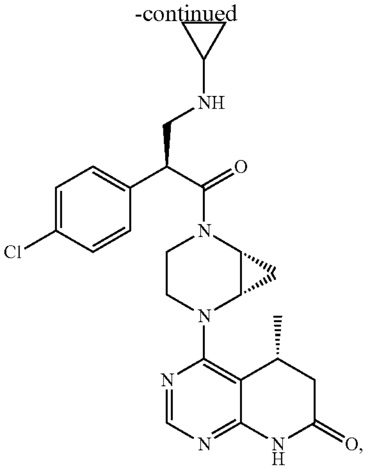

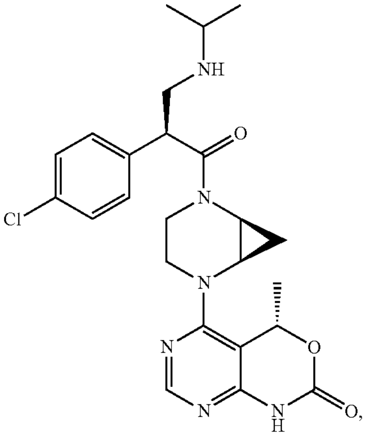

and

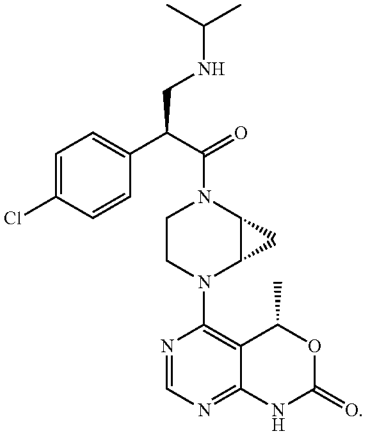

3. The unit dosage pharmaceutical composition according to claim 1, wherein the mass of the compound I-0 or the pharmaceutically acceptable salt of the compound I-0 is 10 mg to 400 mg, or 10 mg to 200 mg, or 10 mg to 150 mg, or 25 mg to 150 mg, or 25 mg to 100 mg, or 10 mg, or 25 mg, or 50 mg, or 75 mg, or 100 mg, or 150 mg, or 200 mg, or 400 mg, calculated as the free base.

4. The unit dosage pharmaceutical composition according to claim 1, wherein calculated as the free base, the mass of the compound I-0 or the pharmaceutically acceptable salt thereof is 0.1-99.9% of the total mass of the unit dosage pharmaceutical composition.

5. The unit dosage pharmaceutical composition according to claim 1, wherein the compound I-0 is a compound I or a pharmaceutically acceptable salt thereof, wherein the mass of the compound I or the pharmaceutically acceptable salt thereof is 5 mg to 400 mg calculated as a free base, and the compound I has the following structure:

I

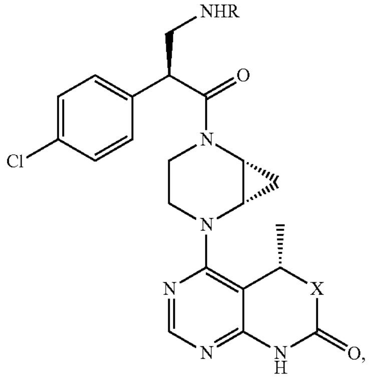

wherein, R is selected from the group consisting of C1-C4 alkyl and C3-C6 cycloalkyl; and X is selected from the group consisting of $CH_2$ and O.

6. The unit dosage pharmaceutical composition according to claim 5, wherein the compound I is selected from the group consisting of:

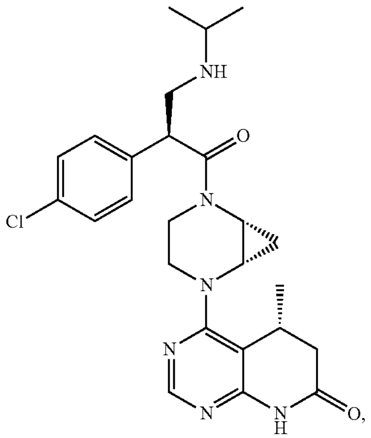

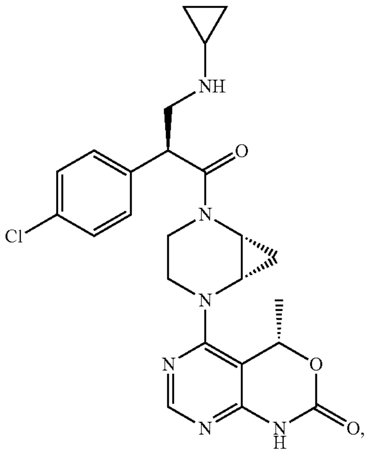

and

-continued

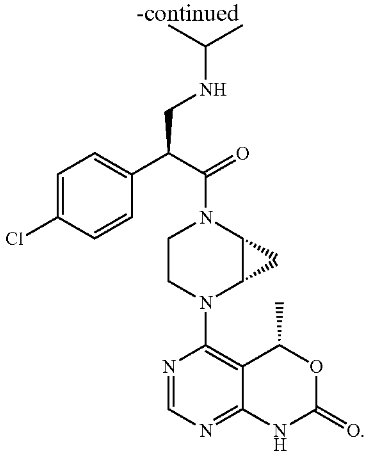

7. The unit dosage pharmaceutical composition according to claim 5, wherein the mass of the compound I or the pharmaceutically acceptable salt thereof is 10 mg to 400 mg, or 10 mg to 200 mg, or 10 mg to 150 mg, or 25 mg to 150 mg, or 25 mg to 100 mg, or 10 mg, or 25 mg, or 50 mg, or 75 mg, or 100 mg, or 150 mg, or 200 mg, or 400 mg, calculated as the free base.

8. The unit dosage pharmaceutical composition according to claim 5, wherein calculated as the free base, the mass of the compound I or the pharmaceutically acceptable salt thereof is 0.1-99.9% of the total mass of the unit dosage pharmaceutical composition.

9. The unit dosage pharmaceutical composition according to claim 1, further comprising one or more pharmaceutically acceptable carriers.

10. The unit dosage pharmaceutical composition according to claim 1, wherein the unit dosage pharmaceutical composition is a pharmaceutical preparation suitable for an oral administration.

11. The unit dosage pharmaceutical composition according to claim 1 for use as a medicament.

12. A method for treating an AKT protein kinase-mediated disease or disease state, wherein the method comprises administering the unit dosage pharmaceutical composition according to claim 1 to a subject in need; wherein, the AKT protein kinase-mediated disease or disease state is a breast cancer, a prostate cancer, or an ovarian cancer.

13. The method according to claim 12, wherein the dosage of the unit dosage pharmaceutical composition administered to the subject in need that is calculated based on the compound I-0 is 0.01-50 mg/kg weight/day.

14. The unit dosage pharmaceutical composition according to claim 1, wherein R is selected from the group consisting of methyl, ethyl, n-propyl, isopropyl, tert-butyl, cyclopropyl, cyclopentyl or cyclohexyl.

15. The unit dosage pharmaceutical composition according to claim 1, wherein X is $CH_2$.

16. The unit dosage pharmaceutical composition according to claim 1, wherein calculated as the free base, the mass of the compound I-0 or the pharmaceutically acceptable salt thereof is 5-90% of the total mass of the unit dosage pharmaceutical composition.

17. The unit dosage pharmaceutical composition according to claim 1, wherein calculated as the free base, the mass of the compound I-0 or the pharmaceutically acceptable salt thereof is 25-65% of the total mass of the unit dosage pharmaceutical composition.

18. The unit dosage pharmaceutical composition according to claim 5, wherein R is selected from the group consisting of methyl, ethyl, n-propyl, isopropyl, tert-butyl, cyclopropyl, cyclopentyl or cyclohexyl.

19. The unit dosage pharmaceutical composition according to claim 5, wherein X is $CH_2$.

20. The unit dosage pharmaceutical composition according to claim 5, wherein calculated as the free base, the mass of the compound I-0 or the pharmaceutically acceptable salt thereof is 5-90% of the total mass of the unit dosage pharmaceutical composition.

21. The unit dosage pharmaceutical composition according to claim 5, wherein calculated as the free base, the mass of the compound I-0 or the pharmaceutically acceptable salt thereof is 25-65% of the total mass of the unit dosage pharmaceutical composition.

* * * * *